United States Patent
Franklin et al.

(10) Patent No.: US 10,631,556 B2
(45) Date of Patent: *Apr. 28, 2020

(54) METHOD FOR CONDUCING CONCENTRATED CANNABIS OIL TO BE STABLE, EMULSIFIABLE AND FLAVORLESS FOR USE IN HOT BEVERAGES AND RESULTING POWDERIZED CANNABIS OIL

(71) Applicant: Pivot Naturals, LLC., Anaheim, CA (US)

(72) Inventors: Ross M. Franklin, Farmers Branch, TX (US); Ed Rosenthal, Oakland, CA (US); Rachel M. Franklin, Farmers Branch, TX (US)

(73) Assignee: PIVOT PHARMACEUTICALS US INC., Seattle, WA (US)

( * ) Notice: Subject to any disclaimer, the term of this patent is extended or adjusted under 35 U.S.C. 154(b) by 19 days.

This patent is subject to a terminal disclaimer.

(21) Appl. No.: 16/195,781

(22) Filed: Nov. 19, 2018

(65) Prior Publication Data

US 2019/0082721 A1    Mar. 21, 2019

Related U.S. Application Data

(63) Continuation-in-part of application No. 15/466,788, filed on Mar. 22, 2017, now Pat. No. 10,172,379,
(Continued)

(51) Int. Cl.
| | |
|---|---|
| A61K 36/00 | (2006.01) |
| A23L 2/395 | (2006.01) |
| A23F 3/40 | (2006.01) |
| A23L 2/56 | (2006.01) |
| A61K 9/00 | (2006.01) |
| A61K 9/14 | (2006.01) |
| A61K 31/352 | (2006.01) |
| A61K 36/185 | (2006.01) |
| A23D 9/02 | (2006.01) |
| A23L 7/143 | (2016.01) |
| A61K 38/02 | (2006.01) |
| A21D 13/44 | (2017.01) |
| A21D 13/80 | (2017.01) |
| A23D 9/05 | (2006.01) |
| A23D 9/007 | (2006.01) |
| A23L 27/10 | (2016.01) |
| A23L 29/30 | (2016.01) |
| A23L 2/52 | (2006.01) |
| A61K 47/44 | (2017.01) |
| A61K 47/38 | (2006.01) |
| A61K 9/20 | (2006.01) |
| A61K 9/48 | (2006.01) |

(Continued)

(52) U.S. Cl.
CPC ............ *A23L 2/395* (2013.01); *A21D 2/36* (2013.01); *A21D 13/44* (2017.01); *A21D 13/80* (2017.01); *A23D 9/007* (2013.01); *A23D 9/02* (2013.01); *A23D 9/05* (2013.01); *A23F 3/405* (2013.01); *A23F 5/465* (2013.01); *A23L 2/38* (2013.01); *A23L 2/52* (2013.01); *A23L 2/56* (2013.01); *A23L 5/00* (2016.08); *A23L 7/143* (2016.08); *A23L 27/10* (2016.08); *A23L 29/35* (2016.08); *A23L 33/105* (2016.08); *A61K 9/0056* (2013.01); *A61K 9/0095* (2013.01); *A61K 9/146* (2013.01); *A61K 9/20* (2013.01); *A61K 9/48* (2013.01); *A61K 31/352* (2013.01); *A61K 36/185* (2013.01); *A61K 38/02* (2013.01); *A61K 47/36* (2013.01); *A61K 47/38* (2013.01); *A61K 47/44* (2013.01); *C11B 9/00* (2013.01); *G01N 33/948* (2013.01); *A23V 2002/00* (2013.01); *A61K 2236/37* (2013.01); *B65D 85/808* (2013.01); *B65D 85/8046* (2013.01); *Y02W 90/11* (2015.05)

(58) Field of Classification Search
CPC ........................................................ A61K 36/00
USPC ........................................................ 424/725
See application file for complete search history.

(56) References Cited

U.S. PATENT DOCUMENTS

| | | |
|---|---|---|
| 5,127,953 A | 7/1992 | Hamaguchi |
| 2004/0033280 A1 | 2/2004 | Whittle |

(Continued)

FOREIGN PATENT DOCUMENTS

| | | |
|---|---|---|
| CN | 104186826 A | 12/2014 |
| EP | 0289069 A2 | 11/1988 |

(Continued)

OTHER PUBLICATIONS

Bowles EJ. The Chemistry of Aromatherapeutic Oils. 3rd edn. Crow's Nest, NSW: Allen & Unwin; 2003 https://www.amazon.com/Chemistry-Aromatherapeutic-Oils-Joy-Bowles/dp/174114051X.

(Continued)

*Primary Examiner* — Michael V Meller

(74) *Attorney, Agent, or Firm* — Lapple Ubell IP Law, LLP; Matthew C. Lapple

(57) ABSTRACT

A method for producing powderized cannabis oil, and the resulting powderized cannabis oil, in which concentrated cannabis oil is mixed with and absorbed by a modified starch powder, preferably maltodextrin, in a ratio of at least three grams of starch powder for every one-eighth of a gram of cannabis oil is disclosed. Further disclosed are beverages, baked goods and single-serve beverage brewing cartridges utilizing or incorporating the powderized cannabis oil to create human-consumable products that contain an emulsified, tasteless, and odorless dose of cannabis oil.

3 Claims, 8 Drawing Sheets

Related U.S. Application Data which is a continuation of application No. 15/049,916, filed on Feb. 22, 2016, now Pat. No. 9,629,886, said application No. 16/195,781 is a continuation-in-part of application No. 15/466,068, filed on Mar. 22, 2017, now Pat. No. 10,165,790, which is a continuation of application No. 15/049,916, filed on Feb. 22, 2016, now Pat. No. 9,629,886, said application No. 16/195,781 is a continuation-in-part of application No. 15/466,808, filed on Mar. 22, 2017, now Pat. No. 10,376,551, which is a continuation-in-part of application No. 15/049,916, filed on Feb. 22, 2016, now Pat. No. 9,629,886.

(60) Provisional application No. 62/120,275, filed on Feb. 24, 2015, provisional application No. 62/650,917, filed on Mar. 30, 2018.

(51) Int. Cl.

| | | |
|---|---|---|
| *A61K 47/36* | (2006.01) | |
| *G01N 33/94* | (2006.01) | |
| *A21D 2/36* | (2006.01) | |
| *A23L 5/00* | (2016.01) | |
| *A23L 33/105* | (2016.01) | |
| *A23L 2/38* | (2006.01) | |
| *A23F 5/46* | (2006.01) | |
| *C11B 9/00* | (2006.01) | |
| *B65D 85/804* | (2006.01) | |
| *B65D 85/808* | (2006.01) | |

(56) References Cited

U.S. PATENT DOCUMENTS

| | | |
|---|---|---|
| 2008/0175902 A1 | 7/2008 | Zajicek |
| 2013/0274321 A1 | 10/2013 | Newland |
| 2016/0143972 A1 | 5/2016 | Stebbins et al. |
| 2016/0243177 A1 | 8/2016 | Franklin et al. |

FOREIGN PATENT DOCUMENTS

| | | |
|---|---|---|
| KR | 1020050021003 A | 3/2005 |
| WO | 2013009928 A1 | 1/2013 |
| WO | 2013138906 A1 | 9/2013 |

OTHER PUBLICATIONS

Buchbauer G. Biological activities of essential oils. In: Baser KHC, Buchbauer G, editors. Handbook of Essential Oils: Science, Technology, and Applications. Boca Raton, FL: CRC Press; 2010. pp. 235-280. https://ttngmai.files.wordpress.com/2012/09/handbookofessentionaloil.pdf.

Adams TB, Taylor SV. Safety evaluation of essential oils: a constituent-based approach. In: Baser KHC, Buchbauer G, editors. Handbook of Essential Oils: Science, Technology, and Applications.Boca Raton, FL: CRC Press; 2010. pp. 185-208 https://www.taylorfrancis.com/books/e/9781466590472/chapters/10.1201%2Fb19393-12.

Russo EB. The solution to the medicinal cannabis problem. In: Schalman ME, editor. Ethical Issues in Chronic Pain Management. Boca Raton, FL: Taylor & Francis; 2006. pp. 165-194 http://cannabisplus.net/cannabis-research-pdf/Pain/Russo%20Solution%20to%20the%20Medicinal%20Cannabis%20Problem%20%28in%20Schatman,%20Ethical%20Problems%20in%20Ethical%20Issues%20in%20Chronic%20Pain%20Management%29.pdf.

Review Human cannabinoid pharmacokinetics. Huestis MA Chem Biodivers. Aug. 2007; 4(8):1770-804. https://www.ncbi.nlm.nih.gov/pmc/articles/PMC2689518/.

Effects of citrus fragrance on immune function and depressive states. Komori T, Fujiwara R, Tanida M, Nomura J, Yokoyama MM Neuroimmunomodulation. May-Jun. 1995; 2(3):174-80. https://www.ncbi.nlm.nih.gov/pubmed/8646568.

D-limonene exposure to humans by inhalation: uptake, distribution, elimination, and effects on the pulmonary function. Falk-Filipsson A, Löf A, Hagberg M, Hjelm EW, Wang Z J Toxicol Environ Health. Jan. 1993; 38(1):77-88. https://www.ncbi.nlm.nih.gov/pubmed/8421324.

Uptake, distribution and elimination of alpha-pinene in man after exposure by inhalation. Falk AA, Hagberg MT, Löf AE, Wigaeus-Hjelm EM, Wang ZP Scand J Work Environ Health. Oct. 1990; 16(5):372-8. https://www.ncbi.nlm.nih.gov/pubmed/2255878.

Jäger W, Buchbauer G, Jirovetz L, Fritzer M. Percutaneous absorption of lavender oil from a massage oil. J Soc Cosmet Chem. 1992;43:49-54. Jan./Feb. https://pdfs.semanticscholar.org/3530/6465958d8e35e36e7933fa57ba134fe4f9b3.pdf.

Inhalation of vapor from black pepper extract reduces smoking withdrawal symptoms. Rose JE, Behm FM Drug Alcohol Depend. Feb. 1994; 34(3):225-9. https://www.ncbi.nlm.nih.gov/pubmed/8033760.

Rochefort C, Gheusi G, Vincent JD, Lledo PM. Enriched odor exposure increases the number of newborn neurons in the adult olfactory bulb and improves odor memory. J Neurosci. 2002;22:2679-2689. https://www.ncbi.nlm.nih.gov/pubmed/11923433.

Delgado P, Moreno F. Antidepressants and the brain. Int Clin Psychopharmacol. 1999;14(Suppl 1):S9-16. https://www.ncbi.nlm.nih.gov/pubmed/10468323.

Gerdeman GL, Lovinger DM. Emerging roles for endocannabinoids in long-term synaptic plasticity. Br J Pharmacol. 2003;140:781-789. https://www.ncbi.nlm.nih.gov/pmc/articles/PMC1574086/.

PCT International Search Report dated Jun. 24, 2016 for International Application No. PCT/IB2016/050961 (International Filing Date Feb. 25, 2016).

PCT Written Opinion of the International Search Authority dated Jun. 24, 2016 for International Application No. PCT/IB2016/050961 (International Filing Date Feb. 25, 2016).

The extended European search report mailed by European Patent Office dated Oct. 2, 2018 in the corresponding European patent application No. 16754829.6—10 pages.

| Time (min) | Water Temp (°F) | Oil Temp (°F) | Notes: |
|---|---|---|---|
| 0.0 | 66 | 66 | Began with 3750mL (approx. 1gal) of tap water in large stock pot; water level approx. 2/3 of the way up the jar of oil. |
| 0.5 | 66 | 66 | |
| 1.0 | 66 | 66 | |
| 1.5 | 66 | 66 | Oil at high viscosity - entire volume near solid consistency. |
| 2.0 | 67 | 66 | |
| 2.5 | 68 | 66 | |
| 3.0 | 69 | 66 | |
| 3.5 | 70 | 66 | |
| 4.0 | 71 | 66 | |
| 4.5 | 72 | 66 | |
| 5.0 | 74 | 66 | No change in oil viscocity. |
| 5.5 | 75 | 66 | |
| 6.0 | 77 | 66 | |
| 6.5 | 78 | 66 | |
| 7.0 | 80 | 66 | |
| 7.5 | 81 | 66 | |
| 8.0 | 83 | 66 | |
| 8.5 | 84 | 66 | |
| 9.0 | 85 | 66 | |
| 9.5 | 86 | 66 | |
| 10.0 | 87 | 66 | No change in oil viscocity. |
| 10.5 | 88 | 66 | |
| 11.0 | 89 | 66 | |
| 11.5 | 90 | 66 | |
| 12.0 | 90 | 66 | |
| 12.5 | 91 | 66 | |
| 13.0 | 93 | 66 | |
| 13.5 | 93 | 66 | |
| 14.0 | 95 | 66 | |
| 14.5 | 96 | 66 | |
| 15.0 | 97 | 66 | Oil beginning to soften at bottom of jar. |
| 15.5 | 99 | 66 | |
| 16.0 | 101 | 66 | |
| 16.5 | 102 | 66 | |
| 17.0 | 103 | 67 | |
| 17.5 | 104 | 67 | |
| 18.0 | 106 | 67 | |
| 18.5 | 107 | 67 | |
| 19.0 | 108 | 67 | |
| 19.5 | 109 | 67 | |
| 20.0 | 110 | 67 | Slight softening of outer layer of oil; center retains consistency of a solid. |
| 20.5 | 111 | 67 | |
| 21.0 | 112 | 68 | |
| 21.5 | 113 | 68 | |
| 22.0 | 114 | 68 | |
| 22.5 | 114 | 68 | |

FIG. 3A

| Time (min) | Water Temp (°F) | Oil Temp (°F) | Notes: |
|---|---|---|---|
| 23.0 | 115 | 68 | |
| 23.5 | 116 | 68 | |
| 24.0 | 117 | 69 | |
| 24.5 | 118 | 69 | |
| 25.0 | 119 | 69 | Moderate softening of outer layer of oil; center remains solid. |
| 25.5 | 120 | 69 | |
| 26.0 | 121 | 69 | |
| 26.5 | 122 | 69 | |
| 27.0 | 123 | 69 | |
| 27.5 | 124 | 69 | |
| 28.0 | 126 | 69 | |
| 28.5 | 127 | 69 | |
| 29.0 | 128 | 69 | |
| 29.5 | 130 | 69 | |
| 30.0 | 131 | 69 | |
| 30.5 | 132 | 70 | Moderate softening of outer layer; center remains solid. |
| 31.0 | 134 | 70 | |
| 31.5 | 134 | 70 | |
| 32.0 | 135 | 70 | |
| 32.5 | 136 | 70 | |
| 33.0 | 137 | 70 | |
| 33.5 | 138 | 70 | |
| 34.0 | 139 | 70 | |
| 34.5 | 139 | 70 | |
| 35.0 | 140 | 70 | Significant softening of outer layer of oil; center remains solid. |
| 35.5 | 141 | 71 | |
| 36.0 | 142 | 71 | |
| 36.5 | 143 | 71 | |
| 37.0 | 143 | 71 | |
| 37.5 | 144 | 71 | |
| 38.0 | 145 | 72 | |
| 38.5 | 146 | 72 | |
| 39.0 | 146 | 72 | |
| 39.5 | 147 | 72 | Significant softening of outer layer; center slightly softening - "melting" appearance. Consistency does not lend itself to stirring at this point. |
| 40.0 | 148 | 73 | |
| 40.5 | 149 | 73 | |
| 41.0 | 150 | 73 | |
| 41.5 | 151 | 73 | |
| 42.0 | 152 | 74 | |
| 42.5 | 153 | 74 | |
| 43.0 | 154 | 74 | |
| 43.5 | 156 | 75 | |
| 44.0 | 157 | 75 | |
| 44.5 | 158 | 75 | |
| 45.0 | 159 | 75 | Significant softening throughout entire volume of oil; outer layer of oil at liquid viscosity. |
| 45.5 | 160 | 76 | |

FIG. 3B

| Time (min) | Water Temp (°F) | Oil Temp (°F) | Notes: |
|---|---|---|---|
| 46.0 | 162 | 76 | |
| 46.5 | 163 | 76 | Gentle stirring of oil now possible to even out |
| 47.0 | 163 | 77 | heat dispersment; oil nearly at optimum viscosity. |
| 47.5 | 164 | 78 | |
| 48.0 | 164 | 78 | Further stirring. |
| 48.5 | 165 | 79 | |
| 49.0 | 166 | 79 | |
| 49.5 | 166 | 82 | |
| 50.0 | 167 | 84 | Optimum viscosity reached. |
| 50.5 | 167 | 88 | |
| 51.0 | 167 | 90 | |
| 51.5 | 168 | 92 | |
| 52.0 | 169 | 94 | |

FIG. 3C

METHOD FOR CONDUCING CONCENTRATED CANNABIS OIL TO BE STABLE, EMULSIFIABLE AND FLAVORLESS FOR USE IN HOT BEVERAGES AND RESULTING POWDERIZED CANNABIS OIL

CROSS REFERENCE TO RELATED APPLICATIONS

The subject application is a continuation-in-part application and claims priority to U.S. Provisional Patent Application Ser. No. 62/120,275, filed on Feb. 24, 2015; U.S. Nonprovisional patent application Ser. No. 15/049,916, filed on Feb. 22, 2016 and issued on Apr. 25, 2017 as U.S. Pat. No. 9,629,886; U.S. Nonprovisional patent application Ser. No. 15/466,068, filed on Mar. 22, 2017; U.S. Nonprovisional patent application Ser. No. 15/466,808, filed on Mar. 22, 2017; U.S. Nonprovisional patent application Ser. No. 15/466,788, filed on Mar. 22, 2017; and U.S. Provisional Patent Application Ser. No. 62/650,917, filed on Mar. 30, 2018; and all of such applications are incorporated herein in their entirety by this reference thereto.

FIELD OF THE DISCLOSURE

The embodiments of the described invention relate generally to methods and compositions of matter for enabling concentrated cannabis oil to be stable, emulsifiable and flavorless for use in hot beverages or food by combining said oil with a starch powder or starch-derived powder. Embodiments also relate to a variety of culinary uses for the stabilized, emulsified, flavorless concentrated cannabis oil powder.

BACKGROUND

Cannabis, also commonly known as marijuana, is a flowering plant that includes three species or sub-species, namely sativa, indica and ruderalis. The plant is indigenous to Central Asia and the Indian Subcontinent. Cannabis has long been used for hemp fiber, for oils, for medicinal purposes and as a recreational drug. Cannabis plants produce a group of chemicals called cannabinoids. The majority of these compounds are secreted by glandular trichomes that occur abundantly on the floral calyxes and bracts of female cannabis plants. When used by humans medicinally or recreationally, cannabis can be consumed by a variety of routes, including vaporizing or smoking dried flower buds and leaf portions, resins, extracted oils or waxes. However, in recent years many medicinal patients, as well as recreational users, have begun to prefer consuming cannabis in edible form, by eating lozenges, candies, or baked goods, drinking beverages, or by taking capsules.

The most well-known cannabinoid is tetrahydrocannabinol, often abbreviated as "THC." The chemical formula for THC is $C_{21}H_{30}O_2$ and it has the following chemical structure:

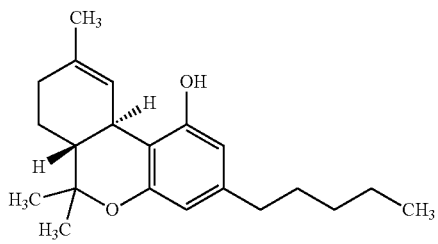 [SMILES: CCCCCc1cc(O)c2c(c1)OC(C)(C)[C@@H]1CCC(C)=C[C@@H]21]

THC is an aromatic terpenoid and is widely recognized as the principal psychoactive constituent in cannabis. THC has a very low solubility in water, but good solubility in most organic solvents, specifically lipids and alcohols.

The cannabis plant produces hundreds of other cannabinoids, terpenoids and other compounds that are only beginning to be identified, studied and categorized. One generally recognized cannabinoid that has medical efficacy is Cannabidiol ("CBD"). It is a major constituent of the plant, second to THC, and represents up to 40% by weight, in its extracts. Compared with THC, CBD is not psychoactive in healthy individuals, and is considered to have a wider scope of medical applications than THC, including for epilepsy, multiple sclerosis spasms, anxiety disorders, bipolar disorder, schizophrenia, nausea, convulsion and inflammation, as well as inhibiting cancer cell growth.

It is also believed by many researchers that many of the other cannabinoids, terpenoids and other compounds may have important health benefits and/or be capable of treating certain human diseases.

There are two characterized cannabinoid receptors in the human body, CB1, which is primarily located in the central nervous system, and CB2 which is primarily located in the immune system and blood cells. These cannabinoid receptors are naturally present and are activated by endocannabinoids that are produced by the human body for neural and cell signaling. In neurons, endocannabinoids bind to the CB1 receptors at the pre-synaptic junction and, among other effects, impact the release of gamma-amino butyric acid ("GABA"). However, when THC is present in the human bloodstream, it binds to these cannabinoid receptors and causes many different psychotropic effects.

Consumption of cannabis by a human generally results in a wide variety of psychotropic effects, but which is often referred to as a "high." The cannabis high varies depending on many factors, including the strain of cannabis, the amount consumed, the method of consumption, the biochemistry of the individual consuming it and the individual's level of experience in consuming cannabis. That said, a cannabis high can include euphoria, anxiety, a general alteration of conscious perception, feelings of well-being, relaxation or stress reduction, increased appreciation of humor, music (especially discerning its various components/instruments) or the arts, joviality, metacognition and introspection, enhanced recollection (episodic memory), increased sensuality, increased awareness of sensation, increased libido, and creativity. Abstract or philosophical thinking, disruption of linear memory and paranoia or anxiety are also typical effects.

Cannabis consumption also often produces many subjective and highly tangible effects, such as greater enjoyment of food taste and aroma, an enhanced enjoyment of music and comedy, and marked distortions in the perception of time and space (where experiencing a "rush" of ideas from the bank of long-term memory can create the subjective impression of long elapsed time, while a clock reveals that only a short time has passed). Many individuals find some of these effects pleasing and enjoyable, while other individuals do not enjoy such effects.

Although cannabis has a high margin of safety, it can produce negative side effects. At higher doses in humans, effects can include altered body image, auditory and/or visual illusions, pseudo-hallucinatory, and ataxia from selective impairment of polysynaptic reflexes. In some cases, in humans, cannabis can lead to dissociative states such as depersonalization and derealization. Additionally, canine studies of very high doses of cannabis resulted in intoxication effects including depression, hypersalivation, mydriasis, hypermetria, vomiting, urinary incontinence, tremors, hypothermia, bradycardia, nystagmus, agitation, tachypnea, ataxia hyperexcitability and seizures. Occasionally, heavy use, or use by inexperienced human consumers, particularly in an unfamiliar environment, can result in very negative experiences. Any episode of acute psychosis that accompanies cannabis use usually abates after 6 hours, but in rare instances heavy users may find the symptoms continuing for many days. If the episode is accompanied by aggression or sedation, physical restraint may be necessary.

While many psychoactive drugs clearly fall into the category of either stimulant, depressant, or hallucinogen, cannabis exhibits a mix of all properties, perhaps leaning the most towards hallucinogenic or psychedelic properties, though with other effects quite pronounced as well. THC is typically considered the primary active component of the cannabis plant.

Cannabis growers have been developing different strains of cannabis plants that have different THC and CBD levels. Recently, medical cannabis users have been demanding medical cannabis products that have CBD as the main active ingredient, and little or no THC, providing some of the medicinal benefits of cannabis without the psychoactive effects caused mainly by THC.

A psychoactive drug, psycho pharmaceutical, or psychotropic is a chemical substance that crosses the blood-brain barrier and acts primarily upon the central nervous system where it affects brain function, resulting in alterations in perception, mood, consciousness, cognition, and behavior. These substances may be used recreationally, to purposefully alter one's consciousness, or as entheogens, for ritual, spiritual, and/or shamanic purposes, as a tool for studying or augmenting the mind. Many psychoactive drugs have therapeutic utility, e.g., as anesthetics, analgesics, or for the treatment of psychiatric disorders.

Psychoactive substances often bring about subjective changes in consciousness and mood that the user may find pleasant (e.g. euphoria) or advantageous (e.g. increased alertness) and are, thus, reinforcing. Thus, many psychoactive substances are abused, that is, used excessively, despite health risks or negative consequences. With sustained use of some substances, psychological and physical dependence ("addiction") may develop, making the cycle of abuse even more difficult to interrupt. Drug rehabilitation aims to break this cycle of dependency, through a combination of psychotherapy, support groups, maintenance and even other psychoactive substances. However, the reverse is also true in some cases, that certain experiences on drugs may be so unfriendly and uncomforting that the user may never want to try the substance again. This is especially true of the deliriants (e.g. Jimson weed) and powerful dissociatives (e.g., *Salvia divinorum*). Most purely psychedelic drugs are considered to be nonaddictive (e.g. LSD, psilocybin, mescaline). "Psychedelic amphetamines" or empathogenentactogens (such as MDA and MDMA) may produce an additional stimulant and/or euphoriant effect and, thus, have an addiction potential.

In the early twentieth century, it became illegal in most of the world to cultivate or possess cannabis. However, within the last decade, some states and nations have begun to legalize the cultivation, possession and use of cannabis for medical purposes. Currently, the use of medical marijuana is decriminalized or legalized in 32 U.S. states. Cannabis is used to reduce nausea and vomiting during chemotherapy, to improve appetite in people with HIV/AIDS, to treat chronic pain, and help with muscle spasms. Other possible medical uses, which are sometimes disputed, include treatment of multiple sclerosis, AIDS wasting syndrome, epilepsy, rheumatoid arthritis, glaucoma, PTSD, depression and generalized anxiety. However, many patients and consumers are hesitant to try or continue to consume cannabis, particularly in public, due to the negative social stigma and negative health effects of smoking cannabis. Accordingly, there is a need to address the negative social stigma and negative health effects of smoking cannabis, while allowing individuals to still be able to consume it for medical reasons and its health benefits.

Further, within the last two years, several states in the United States have legalized or decriminalized the cultivation, possession and use of Cannabis for recreational purposes. Currently, its use for any purpose by individuals over the age of eighteen has been decriminalized or legalized in four states and the District of Columbia.

As such, some sources estimate that there are many more recreational users of cannabis than ever before, including new or otherwise inexperienced consumers of cannabis. Yet, one significant drawback for new recreational cannabis users, as well as medical patients, is the variability in the amount of THC that is present in any given cannabis product, whether it is a smokable product, an oil, or an edible. Because of this variability, it is often difficult for new cannabis users to correctly gauge the appropriate amount of cannabis to consume, and likewise it is often difficult for medical patients to accurately dose themselves with the proper amount of THC, CBD or other cannabinoids to address their symptoms. As such, there is a need for a product that enables a consumer to use an accurate, standardized dose of THC and CBD.

As discussed above, many medical patients and newer consumers of cannabis now prefer to consume cannabis by eating or drinking it, rather than smoking. Frequently, edibles and drinks containing cannabis are made using extracted cannabis oil. However, to date, cannabis experts and companies manufacturing edibles and drinks containing cannabis have had significant difficulty in producing edibles and drinks that did not have a strong cannabis smell or flavor. Many medical patients and novice users find this smell and taste unpleasant, as, depending on the strains used to create the oil, the smell and taste is reminiscent of a skunk, pine needles, herbs, or is strongly plant-like. This taste and smell is frequently masked by the addition of other strong flavors or sugar, yet this also often proves unsatisfactory. This is particularly true when cannabis oil is added to subtly flavored beverages such as coffee or tea. Accordingly, there is a need in the industry to develop a way to make edibles and beverages containing cannabis oil that do not have a strong cannabis smell or taste.

Moreover, due to the solubility characteristics of cannabis oil, cannabis experts and companies manufacturing oils and drinks containing cannabis have had significant difficulty in producing an oil that can be added to a drink in a way that the oil will be emulsified, or in solution, or evenly distributed throughout the drink. In many cases, the cannabis oil separates in water-based drinks, such as coffee or tea, and is unpleasant to drink. Moreover, such separation can lead to a medical patient not receiving an accurate dose, if the patient does not consume the entire drink, particularly the separated oil portion of the drink.

Accordingly, there is a need for a standardized and measurable dosage of THC and CBD in a powder form, a way to enable consumers of cannabis to accurately and repeatably deliver the same dose of THC and CBD to address their medical needs, a more socially acceptable, easier, and more convenient way to consume cannabis than smoking it, a way to render the normally unpleasant tasting concentrated cannabis oil flavorless, a way to fully capitalize on the medical benefits of CBD in cannabis products, to eliminate or minimize the psychoactive effects of THC, if so desired, in cannabis products, or otherwise control the level of THC in a consumable form, a way for users to control the THC intake and its associated effects without the negative health aspects of inhaling smoke, a way to select cannabis products made from sativa strains, indica strains or combination thereof, and that enables users to achieve the synergistic effect of caffeinated coffees or teas with cannabis, which can create a mildly euphoric effect in certain controlled doses.

As investigation and research regarding cannabis and its effects upon human physiology have progressed, greater knowledge and understanding has developed regarding the presence and effects of various non-cannabinoid, aromatic compounds found in cannabis, which are known generally as "terpenes." Many different terpenes may be present in different strains of cannabis, in different concentrations. Indeed, over two-hundred different terpenes have been identified as present in one or more strains of cannabis. In some cases, the presence of different terpenes, in different amounts, will have a meaningful impact on the physical and psychoactive effects that a cannabis consumer will experience. Many believe that certain terpenes have medical benefits. Further, terpenes are believed to be an integral component of the "entourage effect." The "entourage effect" is thought by researchers to be a multifaceted combination of cannabinoids and terpenoids occurring in various measure in a cannabis infused smokable or edible product. The significance of the "entourage effect" is that it is believed that cannabinoids, for example, THC and/or CBD interact more effectively with the CB1 and CB2 receptors in the brain, as well as greater efficacy regarding cannabinoid interaction with the endocannabinoid system in the central nervous system. The absence of this multiplicity of cannabinoids and terpenoids or "entourage effect," as demonstrated by isolated THC or CBD, can result in suboptimal health benefits in human beings, relatively speaking. Moreover, terpenes are known to be present in many different non-cannabis plants and are responsible for many common aromas and tastes. Terpenes are the main aromatic compounds in many plant-derived essential oils. Terpenoids are pharmacologically versatile: they are lipophilic, interact with cell membranes, neuronal and muscle ion channels, neurotransmitter receptors, G-protein coupled (odorant) receptors, second messenger systems and enzymes (Bowles, 2003; Buchbauer, 2010). All the terpenoids discussed herein are "Generally Recognized as Safe," as attested by the US Food and Drug Administration as food additives, or by the Food and Extract Manufacturers Association and other world regulatory bodies. Terpenoid components in concentrations above 0.05% are considered of pharmacological interest (Adams and Taylor, 2010). Mice exposed to terpenoid odors inhaled from ambient air for 1 hour demonstrated profound effects on activity levels, suggesting a direct pharmacological effect on the brain, even at extremely low serum concentrations (examples: linalool with 73% reduction in motility at 4.22 ng·mL-1, pinene 13.77% increase at trace concentration, terpineol 45% reduction at 4.7 ng·mL-1). These levels are comparable to those of THC measured in humans receiving cannabis extracts yielding therapeutic effects in pain, or symptoms of multiple sclerosis in various randomized controlled trials (RCTs) (Russo, 2006; Huestis, 2007). Positive effects at undetectable serum concentrations with orange terpenes (primarily limonene, 35.25% increase in mouse activity), could be explainable on the basis of rapid redistribution and concentration in lipophilic cerebral structures. A similar rationale pertains to human studies (Komori et al., 1995), subsequently discussed. Limonene is highly bioavailable with 70% human pulmonary uptake (Falk-Filipsson et al., 1993), and a figure of 60% for pinene with rapid metabolism or redistribution (Falk et al., 1990). Ingestion and percutaneous absorption is also well documented in humans, 1500 mg of lavender EO with 24.7% linalool (total 372 mg) was massaged into the skin of a 60 kg man for 10 min, resulting in a peak plasma concentration of 100 ng·mL-1 at 19 min, and a half-life of 13.76 min in serum (Jäger et al., 1992). Various terpenes that have been identified as sometimes being present in cannabis include, but are not limited to:

Myrcene, including Beta-Myrcene: The odor of Myrcene is variously described as clove-like, earthy, nutty, green-vegetative and citrus-like. Myrcene is also present in large concentrations in hops, lemon grass, the West Indian Bay tree, verbena, and mangos, and particularly in slightly overripe mangos. Myrcene is believed to be a potent analgesic, anti-inflammatory and antibiotic. Myrcene is also believed to be a synergist to THC, and may create a stronger psychoactive effect/experience than THC alone. Myrcene also may affect the permeability of cell membranes and either enable THC to cross the blood-brain barrier more effectively, or serve as a carrier of the THC molecule in this action. Myrcene is also believed to be responsible for the sleepy or relaxed feeling associated with the consumption of some strains of cannabis, and is believed by some to contribute to the "couch-lock" effect of some strains of cannabis.

Limonene: Limonene is found in the rind of citrus fruits, such as lime and lemon, as well as many other fruits and flowers. The odor of Limonene is commonly described as citrus, lime or lemony. Limonene is believed to have anti-bacterial, anti-fungal and anti-cancer activities. It is believed to inhibit the Ras cancer gene cascade which promotes tumor growth. In humans, Limonene quickly permeates the blood-brain barrier and promotes the absorption of other terpenes, as well as an increase in systolic blood pressure. Limonene is variously associated with and believed to be responsible for cannabis consumer's feelings of alertness, restlessness, increased sexuality, buoyancy and focused attention.

Caryophyllene, including Beta-Caryophyllene ("B-Caryophyllene") and Trans-Caryophyllene: Caryophyllene is described as having a sweet, woody, dry-clove odor. Caryophyllene's taste is described as pepper-spicy with camphor and astringent citrus backgrounds. Caryophyllene is found in black pepper, cloves, and cotton, as well as in other herbs and spices. When ingested in large amounts, B-Caryophyllene may block calcium and potassium ion channels. As a result, it may impede pressure exerted by heart muscles. Applied topically, B-Caryophyllene is an analgesic and one of the active constituents of clove oil, a natural and preferred treatment for toothache. It may also help reduce inflammation. Among cannabis consumers, B-Caryophyllene is believed to be responsible for good or positive feelings and slight giddiness.

Pinene, including Alpha-Pinene and Beta-Pinene: Pinene is the familiar odor associated with pine trees and their resins. Pinene is the major component in turpentine (note that the archaic spelling of "terpentine" gives the entire class of aromatic terpenes its name). Pinene is also commonly found in rosemary, sage and eucalyptus. Pinene is sometimes used as an expectorant and a topical antiseptic. It easily crosses the blood-brain barrier and is believed to act as an acetylcholinesterase inhibitor, resulting in improved memory. Pinene is also believed to be a bronchodilator. Pinene is likely to strongly contribute to, or create, the "skunk" odor that is often associated with cannabis. Among cannabis consumers, Pinene is believed to increase focus, self-satisfaction, and energy.

Terpineol: Terpineol has a lilac, citrus, lime or apple blossom odor and is also often perceived as slightly sweet smelling. It is a minor constituent in many plant essential oils and is sometimes used in perfumes and soaps. Terpineol is believed to result in reduced motility, or capability for movement, and has done so in certain rat studies. Among cannabis consumers, Terpineol may account for the reduced motility effect ("couch-lock") associated with some strains of cannabis. The odors of Terpineol in cannabis are often masked by the stronger odors of Pinene, which is often present in the same strains.

Borneol: Borneol has a menthol or camphor-like aroma. It is found in many plants, but is most commonly derived from *Artemisia* (also commonly known as "Wormwood") and some species of Cinnamon. Borneol is a calming sedative in Chinese medicine. Borneol may be responsible for both a calming effect and a psychedelic effect among cannabis consumers.

Delta-3-Carene: Delta-3-Carene has a sweet, pungent odor. It is found in many plants, including in pine and cedar resins and rosemary. Delta-3-Carene may cause drying or cessation of certain body fluids, such as tears and mucus. Delta-3-Carene may contribute to the dry eye and dry mouth effects experienced by some cannabis consumers.

Linalool: Linalool has a floral odor reminiscent of spring flowers such as Lilly-of-the-Valley, but with spice overtones. It is found in lavender and a number of other plants. Linalool is being tested as a cancer treatment. Linalool is believed to have a sedative effect.

Pulegone: Pulegone has a minty-camphor odor and flavor and is used in the candy industry. In very high dosages it is implicated in liver damage. Pulegone is found in very small concentrations in cannabis, but is believed to be an acetylcholinesterase inhibitor, and may partially counteract THC's effect of lowering acetylcholine levels.

Cineole, including 1.8-Cineole or Eucalyptol: Cineole has a camphor-minty odor and is the main component in oil of eucalyptus. Cineole is believed to increase circulation and provide topical pain relief. Cineole, like eucalyptus oil, may contribute to the feelings of centering, balancing, stimulating and thought-provoking experienced by some cannabis consumers.

Ocimene: Ocimene is recognized by its sweet, fragrant, herbaceous, and woodsy aromas. Ocimene is also found in botanicals as diverse as mint, parsley, pepper, basil, mangoes, orchids, cumquats and cannabis. Ocimene is believed to act as an antiviral, an antifungal, an antiseptic, a decongestant and an antibacterial.

Terpinoline: Terpinoline is characterized by a fresh, piney, floral, herbal and occasionally citrusy aroma and flavor. Terpinoline is also found in nutmeg, tea tree, certain confers, apples, cumin and lilacs. Terpinoline is believed to act as an anticancer agent, an antioxidant, a sedative, an antibacterial and an antifungal.

Guaiol: Guaiol is not an oil, but a sesquiterpenoid alcohol, and is also found in cypress pine and guaiacum. Guaiol has been used in traditional medicine as a treatment for diverse ailments ranging from coughs to constipation to arthritis. It is also used as an insect repellent and insecticide. It is believed that Guaiol has antimicrobial and anti-inflammatory properties.

Bisabolol, including A-Bisabolol or Levomenol: Bisabolol is a fragrant terpene that is also found in the chamomile flower and the candeia tree. Bisabolol is believed to be an anti-inflammatory, an anti-irritant, an antioxidant, an anti-microbial, and an analgesic.

Nerol/Nerolidol: Nerol has a subdued and nuanced floral aroma with notes of fruity citrus, apples and rose. It is also found in many strong aromatic plants such as jasmine, tea tree and lemongrass. Nerol is believed to produce sedating effects and may be an antiparasitic, an antifungal, an antimicrobial and is specifically believed to inhibit the growth of leishmaniasis, a parasitic disease spread by the bite of certain types of sandflies.

Humulene: Humulene has a subtle earthy, woody aroma with spicy herbal notes. It is also found in cloves, basil, and hops. It is believed to suppress hunger and is also believed to be an anti-bacterial, an anti-inflammatory, an anti-tumor agent, and a pharmacokinetic.

Geraniol: Geraniol provides the distinctive and delicate aroma of geranium flowers and is sometimes described as smelling like citronella, roses, passionfruit or stonefruit such as peaches or plums. Geraniol is also found in a wide range of plants including tobacco, lemons. Interestingly it is also produced and used by honey bees as a chemical marker or signal. Geraniol is believed to be an antioxidant, an anti-tumor agent, a neuroprotectant, an anti-bacterial, an antifungal and an antispasmodic.

Valencene: Valencene has citrusy sweet aromas and flavors of oranges, grapefruits, tangerines and occasionally of fresh herbs or freshly cut wood. Valencene derives its name from the fact that it is commonly found in Valencia oranges. It is a known repellent of ticks and mosquitos. Valencene is believed to be an anti-inflammatory and an insecticide Thujone: Thuj one has a menthol odor. Thuj one is found in a number of plants, such as arborvitae (genus *Thuja*, hence the derivation of the name), Nootka cypress, some junipers, mugwort, oregano, common sage, tansy, and wormwood, most notably grand wormwood (*Artemisia absinthium*), usually as a mix of isomers in a 1:2 ratio. It is also found in various species of Mentha (mint). Though it is best known as a chemical compound in the spirit absinthe, which contains only small quantities of Thuj one, it is unlikely to be responsible for absinthe's alleged psychedelic effects. Thuj one acts on GABA as an antagonist (opposite to the effects of alcohol) and as a component of several essential oils, is also used in perfumery. As a competitive antagonist of GABA, Thuj one alone is considered to be convulsant, though by interfering with the inhibitory transmitter GABA, it may convey stimulating, mood elevating effects at low doses.

Moreover, terpenes can be used to derive related alcohols, aldehydes or ketones, referred to as "terpenoids" or "isoprenoids," by the addition of further functional groups, most commonly containing Oxygen. As used herein, the term "terpene" or "terpenes" refers to any known terpene, including but not limited to terpenoids or isoprenoids derived therefrom.

Terpenoids can provide adjunctive support. In a clinical trial, 48 cigarette smokers inhaled vapor from an EO of black pepper (*Piper nigrum*), a mint-menthol mixture or placebo (Rose and Behm, 1994). Black pepper EO reduced nicotine craving significantly (P<0.01), an effect attributed to irritation of the bronchial tree, simulating the act of cigarette smoking, but without nicotine or actual burning of material, suggesting a pharmacological effect. The terpenoid profile of black pepper suggests possible candidates: myrcene via sedation, pinene via increased alertness, or especially caryophyllene via CB, agonism and a newly discovered putative mechanism of action in addiction treatment. Results obtained in human depression solely with a citrus scent (Komori et al., 1995), strongly suggest the possibility of synergistic benefit of a phytocannabinoid-terpenoid preparation. Enriched odor exposure in adult mice induced olfactory system neurogenesis (Rochefort et al., 2002), an intriguing result that could hypothetically support plasticity mechanisms in depression (Delgado and Moreno, 1999), and similar hypotheses with respect to the ECS in addiction treatment (Gerdeman and Lovinger, 2003). Phytocannabinoid-terpenoid synergy might theoretically apply. Compelling confirmatory evidence in humans was provided in a clinical study (Komori et al., 1995), in which hospitalized depressed patients were exposed to citrus fragrance in ambient air, with subsequent normalization of Hamilton Depression Scores, successful discontinuation of antidepressant medication in 9/12 patients and serum evidence of immune stimulation (CD4/8 ratio normalization).

It is generally known that the concentrations of different terpenes are highly variable among different strains of cannabis. It is believed that these differences contribute, in part, to the variations in aroma, taste, physical, and psychoactive effects among different strains of cannabis.

It is also generally known that the concentrations of different terpenes, even in the same strain, can be highly variable based on cultivation practices, harvesting times, and post-harvest treatment of cannabis plants. For example, it is believed that the presence of and concentration of terpenes in cannabis can be influenced or manipulated by watering regimes, light exposure, light intensity, growing time, nutrient and mineral delivery regimes and amounts, harvest timing (e.g. how long a plant is allowed to grow before harvest), the amount of time taken to harvest (e.g., labor or equipment limitations may cause large growing operations to take long as 2-4 weeks between when the first plants are harvested and the last plants are harvested), and post-harvest treatment, (e.g., drying and curing vs. flash freezing of green materials).

It is also generally known that the processes of cannabis oil extraction and post-extraction processing of cannabis oil or resin frequently result in the evaporation or destruction of some amount of the terpenes present in the harvested cannabis plant material. Most terpenes have a relatively low boiling point and evaporate easily. Extraction processes that use hydrocarbon-based solvents normally require heating or distillation to remove those solvents, resulting in evaporation of at least some, and often most, terpenes present in the harvested plant material. Extraction processes that use supercritical CO2 are typically better suited to preserve terpenes, but can also result in terpene removal or destruction. Indeed, in some known extraction and distillation processes, terpenes are removed at earlier or later stages of the process than the extraction of the cannabinoids, and are then sometimes recombined with the resultant oil, with mixed results.

Still further, processes used in the manufacture of cannabis oil infused drinks and edibles can result in additional evaporation or destruction of terpenes. Generally, as discussed herein, in its natural form, cannabis produces an acid known as THCA, which is a precursor to THC, but which by itself is not psychoactive. When exposed to heat or certain chemicals, the carboxyl group is removed from THCA, resulting in the psychoactive compound THC. This is generally referred to as "decarboxylation." Therefore, in order for an edible product made with extracted oil to have THC, the oil, either before or after manufacture of the edible, must be decarboxylated. The application of heat during this process can also result in the evaporation or destruction of terpenes. As such, an edible product, such as a candy, that is described as having extracted cannabis oil from a particular strain of cannabis may have a terpene profile that is very different from the terpene profile of that strain when it is consumed by smoking.

Thus, through differences in strains, cultivation practices, harvesting practices, post-harvesting practices, cannabis oil extraction practices and post-extraction processing practices, there are tremendous variability and losses of terpenes in resulting extracted cannabis oil. These differences create problems and issues for manufacturers of cannabis oil infused products and consumers of these products. Manufacturers often have difficulty achieving product consistency and quality control targets due to the inconsistency and variability of the extracted cannabis oil—with respect to terpene types and concentrations—that the manufacturers receive from extracted oil suppliers. Similarly, consumers often experience variability and inconsistency in the taste and effects of branded cannabis-infused products, due to variability in terpene profiles, resulting in consumer confusion, unhappiness and loss of brand loyalty.

As such, there is a need for a method and resulting composition of matter that enables manufacturers of cannabis oil infused products to achieve a consistent terpene profile in their products, regardless of the extracted cannabis oil available. Moreover, there is a need for a method and resulting composition of matter that enables manufacturers of cannabis oil infused products to modify and manipulate the terpene profile of their products, regardless of the terpene profile of the cannabis oil that is available to the manufacturer.

The cannabinoid Tetrahydrocannabivarin ("THCV") is a phyto-cannabinoid that is a naturally occurring plant chemical found in the cannabis plant. THCV and its corresponding acid form ("THCVA", herein collectively "THCV") have been shown to help as an appetite suppressant. Further, THCV has been shown to treat diabetes in some animal studies. THCV is a homologue of THC having a propyl (3-carbon) side chain instead of a pentyl (5-carbon) group on the molecule. THCV is not psychoactive in low doses, but may be in higher doses. THCV may be isolated in an oil extraction process.

SUMMARY OF THE INVENTION

Embodiments of the present invention address the needs described above and relate to making concentrated cannabis oil stable, emulsifiable and flavorless through the addition and mixing of a human consumable powder as discussed herein, particularly a modified starch powder, such as for example, maltodexterin. This concentrated cannabis oil infused powder is effective as a food and beverage additive and could have a high CBD level and a wide range of THC levels, depending on the desired outcome. This concentrated cannabis oil powder can provide users an option to decide the level of acceptable psychoactive effects caused mainly by THC, while getting the medical benefits of CBD.

Other embodiments address the needs described above and relate to making a concentrated cannabis oil powder, and concentrated terpene oil powder, which can be combined to manipulate or standardize the terpene profile of extracted concentrated cannabis oil powder, regardless of the variabilities in terpene profile resulting from differences in strains, cultivation practices, harvesting time, harvesting practices, post-harvesting practices, oil extraction practices and post-extraction practices.

One object and advantage of the present invention is to provide a standardized and measurable dosage of THC and CBD in a powder form, to enable consumers of cannabis to accurately and repeatedly deliver the same dose of THC and CBD to address their medical needs.

Another object and advantage of the present invention is to provide a more socially acceptable, easier, and more convenient way to consume cannabis than smoking it.

Another object and advantage of the present invention is to render the normally unpleasant tasting concentrated cannabis oil flavorless.

Yet another object and advantage of the present invention is to provide a way to fully capitalize on the medical benefits of CBD in cannabis products.

Yet another object and advantage of the present invention is to eliminate or minimize the psychoactive effects of THC, if so desired, in cannabis products, or otherwise control the level of THC in a consumable form.

Yet another object and advantage of the present invention is to provide a way for users to control the THC intake and its associated effects without the negative health aspects of inhaling smoke.

Yet another object and advantage of the present invention is to provide a way to select cannabis products made from sativa strains, indica strains or combination thereof.

Yet another object and advantage of the present invention is to provide a method and compound that enables users to achieve the synergistic effect of caffeinated coffees or teas with cannabis, which can create a mildly euphoric effect in certain controlled doses.

The cannabis oil powder of the present invention is effective for use in applications of hot beverages such as coffees and teas, in single serve beverage brewing cartridges (often referred to as a "K-Cup", which by the registered trademark of Keurig Green Mountain, Inc.) bottled beverages, food/beverage additive packets intended to be poured directly into hot beverages, tea bags, coffee pods/filters, ground coffee and instant coffee forms, as well as in recipes for baked goods or hot foods, where there is a need for different controlled levels of CBD and THC. Additionally, the cannabis oil powder of the present invention lends itself to encapsulation and can be ingested orally in either pill or powder form.

Yet another object and advantage of the present invention is to provide a method, compound, and tablet or capsule that delivers both a dose of THC and/or CBD in combination with a powdered dietary supplement, such as Piperine or powdered Hops, that can enhance the effectiveness of the THC and/or CBD, or reduce perceived negative effects of THC and/or CBD.

Yet another object and advantage of embodiments described herein is the ability to create a powderized cannabis oil that has a modified terpene profile, in order to either address inconsistencies in terpene profiles in extracted oils, to reintroduce terpenes lost during processing, or to custom-blend new terpene profiles for powderized cannabis oil. Such terpenes can be either derived from cannabis plant material, or derived from other non-cannabis sources.

Yet another object and advantage of embodiments described herein is the ability to create a powderized cannabis oil that has enhanced or reintroduced amounts of certain minor cannabinoids, such as, but not limited to THCV.

BRIEF DESCRIPTION OF THE DRAWINGS

In the descriptions that follow, like parts or steps are marked throughout the specification and drawings with the same numerals, respectively. The drawing figures are not necessarily drawn to scale and certain figures may be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein:

FIG. 3A is a table showing the temperatures of one pound of cannabis oil and the water of a water bath, varying over time, during the warming step of an embodiment of the process for powderization of cannabis;

FIG. 3B is continuation of the table of FIG. 3A, showing the temperatures of one pound of cannabis oil and the water of a water bath, varying over time, during the warming step of an embodiment of the process for powderization of cannabis;

FIG. 3C is continuation of the table of FIGS. 3A and 3B, showing the temperatures of one pound of cannabis oil and the water of a water bath, varying over time, during the warming step of an embodiment of the process for powderization of cannabis.

DETAILED DESCRIPTION OF THE PREFERRED EMBODIMENTS

The description that follows is presented to enable one skilled in the art to make and use the present invention, and is provided in the context of a particular application and its requirements. Various modifications to the disclosed embodiments will be apparent to those skilled in the art, and the general principles discussed may be applied to other embodiments and applications without departing from the scope and spirit of the invention. Therefore, the invention is not intended to be limited to the embodiments disclosed, but the invention is to be given the largest possible scope which is consistent with the principles and features described herein.

Embodiments of the present invention relate to the process of extracting concentrated cannabis oil from cannabis plant materials and then combining concentrated cannabis oil with a starch powder, such as maltodextrin, to create a concentrated cannabis oil powder. The resulting cannabis oil powder may be used to dose any edible or beverage so that a patient or recreational user can consume an accurately measured dose of THC or CBD. The resulting cannabis oil powder is generally odorless and tasteless when added to edibles and drinks. Moreover, the resulting cannabis oil powder emulsifies quickly and easily in hot beverages, thereby overcoming the historic problem of separation of cannabis oil and water when cannabis oil is added directly to beverages.

Figure 1:
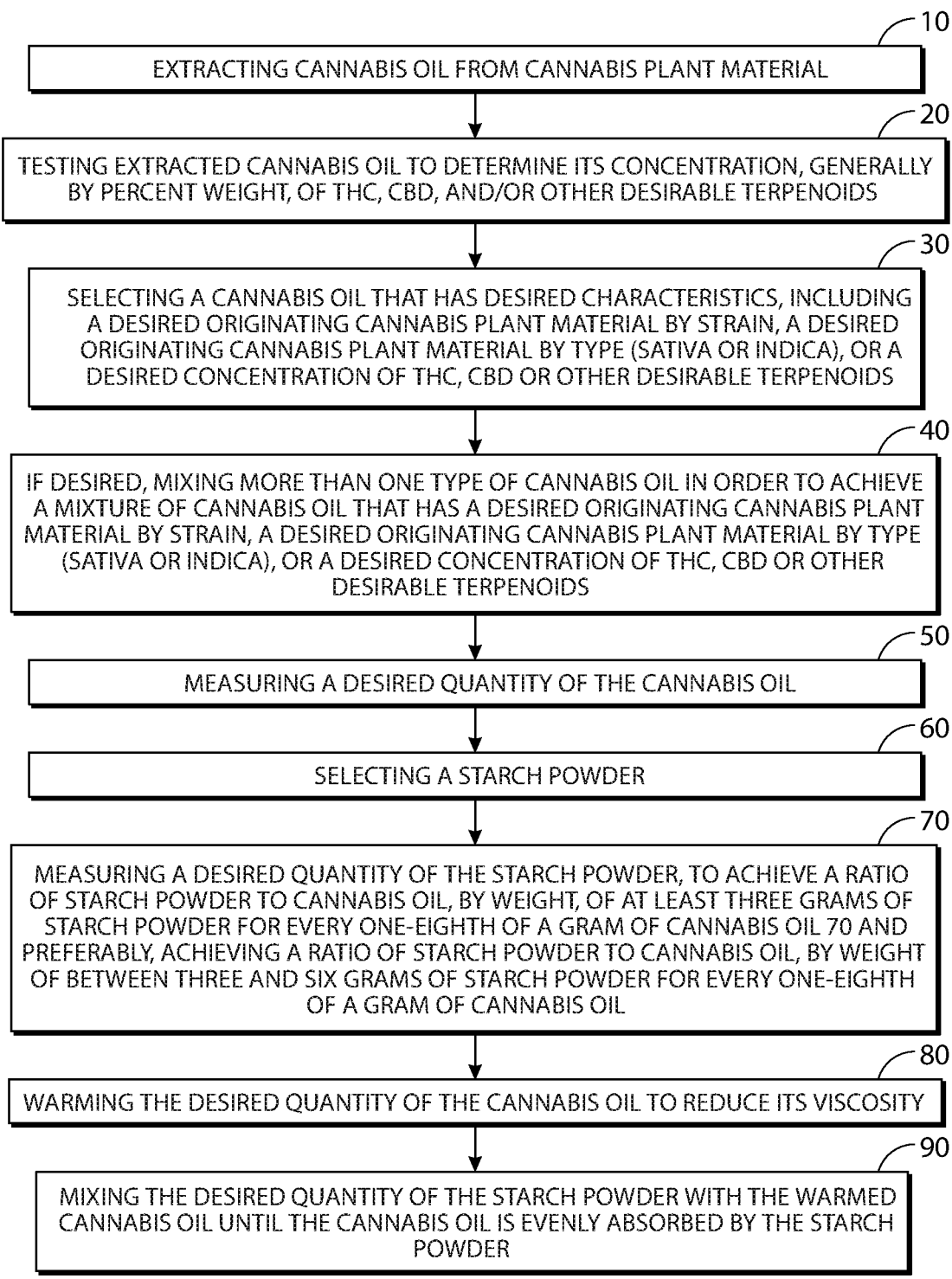
FIG. 1 is a flowchart of an embodiment of the process for powderization of cannabis.
Figure 2:
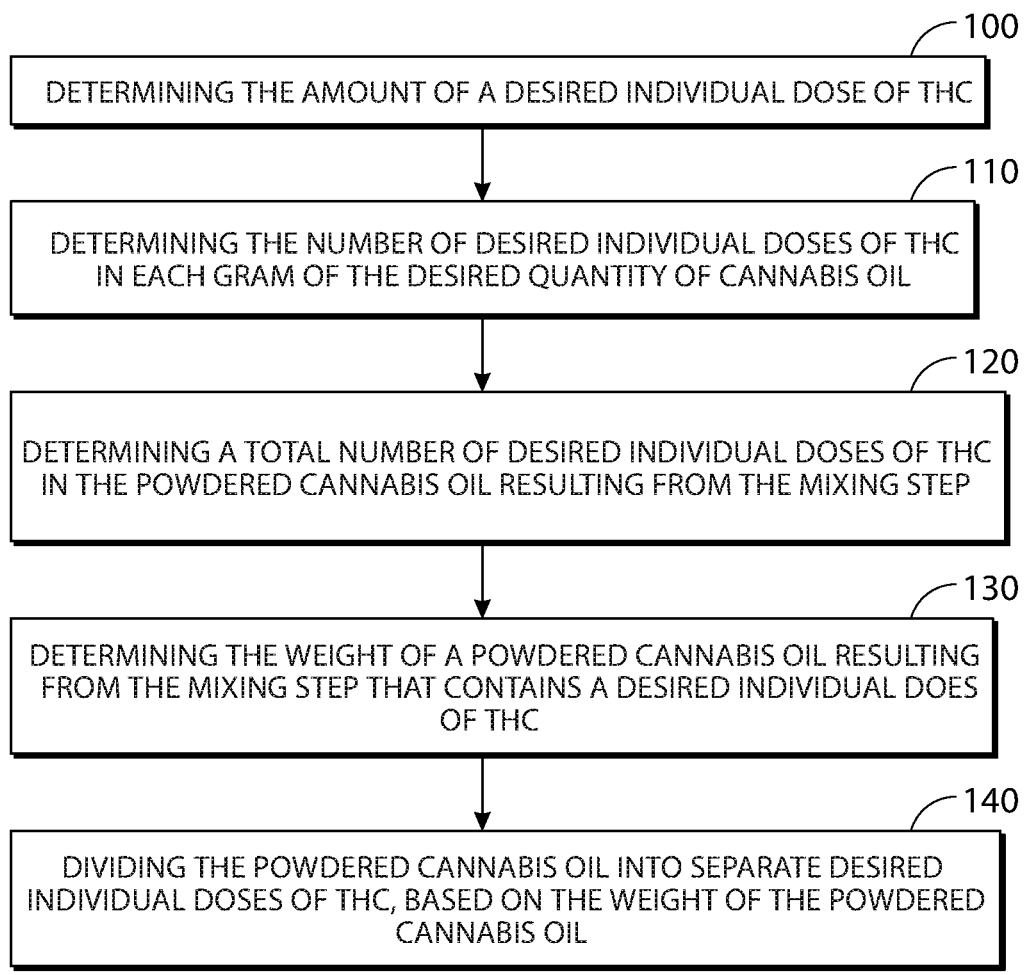
FIG. 2 is a flowchart of further steps in an embodiment of the described powderization process.
Figure 4:
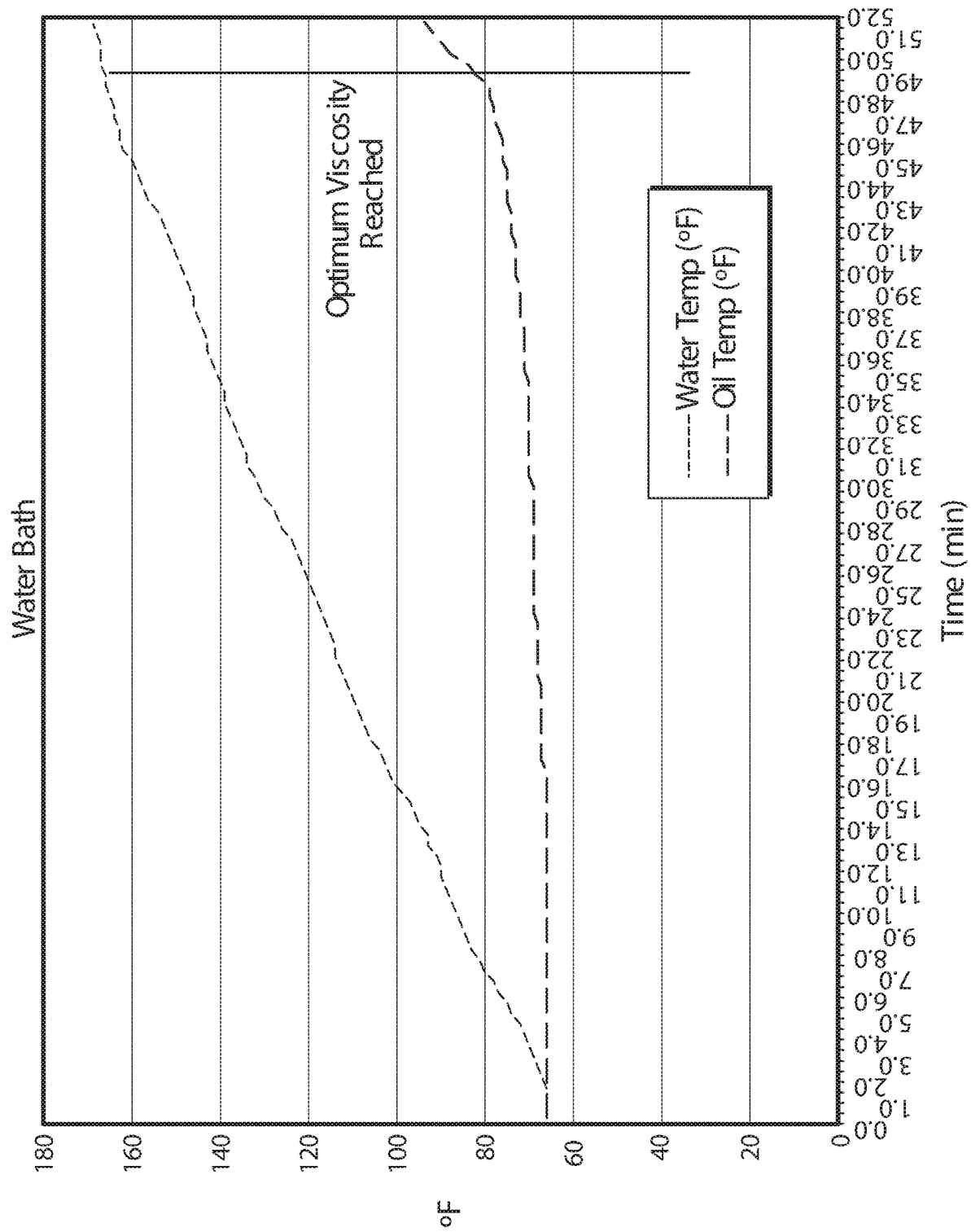
FIG. 4 is a graph showing the relationship of the temperatures of a quantity of cannabis oil and the water of a water bath, varying over time, during the warming step of an embodiment of the process for powderization of cannabis.

Referring to FIG. 1, an embodiment of the process generally includes the following steps:
(a) extracting cannabis oil from cannabis plant material 10;
(b) testing extracted cannabis oil to determine its concentration, generally by percent weight, of THC, CBD, and/or other desirable terpenoids 20;
(c) selecting a cannabis oil that has desired characteristics, including a desired originating cannabis plant material by strain, a desired originating cannabis plant material by type (sativa or indica), or a desired concentration of THC, CBD or other desirable terpenoids 30;
(d) if desired, mixing more than one type of cannabis oil in order to achieve a mixture of cannabis oil that has a desired originating cannabis plant material by strain, a desired originating cannabis plant material by type (sativa or indica), or a desired concentration of THC, CBD or other desirable terpenoids 40;
(e) measuring a desired quantity of the cannabis oil 50;
(f) selecting a starch powder 60;
(g) measuring a desired quantity of the starch powder, to achieve a ratio of starch powder to cannabis oil, by weight, of at least three grams of starch powder for every one-eighth of a gram of cannabis oil 70 and preferably, achieving a ratio of starch powder to cannabis oil, by weight, of between three and six grams of starch powder for every one-eighth of a gram of cannabis oil;
(h) warming the desired quantity of the cannabis oil to reduce its viscosity 80;
(i) mixing the desired quantity of the starch powder with the warmed cannabis oil until the cannabis oil is evenly absorbed by the starch powder 90;

Preferably, embodiments of the process also include the following steps shown in FIG. 2:
(j) determining the amount of a desired individual dose of THC 100;
(k) determining the number of desired individual doses of THC in each gram of the desired quantity of cannabis oil 110;
(l) determining a total number of desired individual doses of THC in the powdered cannabis oil resulting from the mixing step 120;
(m) determining the weight of a powdered cannabis oil resulting from the mixing step that contains a desired individual does of THC 130;
(n) dividing the powdered cannabis oil into separate desired individual doses of THC, based on the weight of the powdered cannabis oil 130.

Several variations of the above process exist and are included in the scope of this disclosure. Likewise, although the above steps are a preferred embodiment, not all of the above steps are required to practice the present invention, except as limited by the claims set forth below.

Concentrated Cannabis Oil

Concentrated cannabis oil is made from cannabis plants. Each cannabis strain has a particular cannabinoid (including CBD and THC) profile. Preferably, the concentrated cannabis oil used in the cannabis oil powder of the present invention is extracted from cannabis plants using any number of different extraction processes, discussed below. Depending on the combination of cannabis strains that the concentrated cannabis oil is made from, each batch of concentrated cannabis oil has a different CBD vs. THC ratio, which will be used for different variants of the present invention. Besides the CBD and THC content, concentrated cannabis oil used in the present invention also takes into account the perceived psychoactive effects of the species of cannabis plants used, particularly cannabis sativa and cannabis indica which are both annual herbaceous plants in the cannabis genus. The perceived effects of sativa are well known for its cerebral high, hence it is often used during the daytime as medical cannabis, while indica is perceived as having sedative effects which some prefer for nighttime use. A careful and skillful selection process of cannabis strains is conducted to ensure the concentrated cannabis oil yielded from the extraction, or the concentrated cannabis oil selected from many different batches of extractions, has a particular CBD:THC ratio range and a desirable sativa and indica proportion.

Each batch of concentrated cannabis oil yielded from extraction preferably is sent to a laboratory so that its CBD and THC level can be tested using the liquid chromatography method. Liquid chromatography mass spectrometry (LC-MS, or alternatively HPLC-MS) is an analytical chemistry technique that combines the physical separation capabilities of liquid chromatography (or HPLC) with the mass analysis capabilities of mass spectrometry (MS). Results of the LC-MS test will indicate CBD and THC content by weight in each batch of concentrated cannabis oil. Moreover each batch of concentrated cannabis oil preferably will go through a phenol analysis to determine the phenol level. If desired, various batches of concentrated cannabis oil may be mixed to achieve a mixture that has the desirable CBD:THC ratio and sativa vs. indica proportion. Separation of CBD from THC is also possible during the extraction process, when it is performed using $CO_2$ extraction, and THC and CBD may be blended to attain a desired ratio of CBD to THC.

Modified Starch Maltodextrin

Maltodextrin is a polysaccharide that is used as a food additive. It is produced from starch by partial hydrolysis and is usually found as a white hygroscopic spray-dried powder. Maltodextrin is easily digestible, being absorbed as rapidly as glucose, and might be either moderately sweet or almost flavorless. It is commonly used for the production of sodas and candy. It can also be found as an ingredient in a variety of other processed foods. Maltodextrin consists of D-glucose units connected in chains of variable length. Maltodextrin can be enzymatically derived from any starch. Maltodextrin has no flavor. Maltodextrin has a glycemic index ranging from 85 to 105.

Manufacturing Process

While the manufacturing process for cannabis oil powder may begin with extraction of the concentrated cannabis oil, and a CO2 extracted oil is preferred, commercially available cannabis oil may also be obtained.

To manufacture the cannabis oil powder, first, concentrated cannabis oil with a particular desired THC:CBD ratio and sativa vs. indica or hybrid of the two, proportion is selected. Selections will be based on demand and cyclical availability of plant trimmings related to different harvest seasons. If the desirable THC:CBD ratio concentrated cannabis oil is not available, a few concentrated cannabis oils of different THC:CBD ratios may be mixed to attain the desirable levels.

Extraction

The powderization of cannabis begins with cannabis extract in the form of oil. Essential oils and waxes are extracted from the cannabis plant into their raw, concentrated form. These extracted oils can then be powderized by adding starch-based emulsifiers such as maltodextrin. Extracted oils are preferable as a base material because of their higher, concentrated THC/CBD content, their properties lend themselves to powderization, and they produce a diminished presence of plant-like tastes and flavors common in edibles infused with other forms of cannabis.

There are numerous ways to extract the essential oils from the cannabis plant. The two most common methods of separating oils and waxes from plant material are mechanical/physical separation and chemical/solvent extraction. Both methodologies have pros and cons regarding time, cost, and potential yields. One thing all methods of extraction have in common is that the resultant yields always depend upon the original condition and quality of the plant material and how it was grown.

Mechanical separation typically involves the use of a screen or filter and cold temperatures. Cold temperatures freeze the tiny trichomes located on plant leaves. Trichomes contain most of the essential oils and waxes intended for extraction. When these trichomes are frozen (typically with ice water or dry ice), they become brittle and break off (separate) from the leaf material. These separated trichomes are then filtered from the leaf material, leaving what is referred to as hash or kief. These materials have a crumbly texture and do not lend themselves to powderization, so this hash product must then be post-processed using a solvent such as ethanol in order to create an oily, fluid consistency. This method, involving the use of ethanol as a solvent, is often referred to as the "Rick Simpson Oil" method, or RSO. Ingesting any solvent, even alcohol, is dangerous so, before consumption, the ethanol must be removed. This can be done by simple evaporation, accelerated by the addition of heat. A rotary evaporator is the best tool for this job due to the ability to keep temperatures relatively low and preserve flavor and terpenes. This process of ice-water extraction is laborious and time consuming and is not a preferred way to obtain concentrates.

Chemical/solvent separation is the preferred method of extraction over mechanical separation because this method returns higher yields, however, the type of solvent is of the utmost importance. Using highly combustible chemical solvents such as butane and propane are rapidly becoming outmoded methods of extraction. They are dangerous during the manufacturing process and if not carefully removed from the resulting oil, they are dangerous to consume. In some cases, these manufacturing methods are becoming outlawed. In addition, post-processing is absolutely critical to ensure the complete removal of the harmful and potentially poisonous solvents.

The safest, cleanest way to extract essential oils from the cannabis plant is to use a CO2 extractor. This type of extraction chamber uses highly pressurized "supercritical" and "subcritical" carbon dioxide gas to pull oils and resins from plant matter. Pressurized CO2 is non-flammable, non-toxic, and though it acts just as a hydrocarbon solvent or organic-chemical solvent would in removing the resinous compounds from cannabis leaf material, CO2 leaves no residual solvent behind. The resulting oils and waxes are solvent-free and generally do not require post-processing. CO2 extractors also keep much of the plant's biochemical properties intact, producing a concentrated oil that generally contains the same properties as when the oil was growing in bud form. Another unique benefit to using this method is its customization capabilities. Depending on the original biochemical makeup of the plant material, using CO2 extraction chambers allow the manufacturer to create an output with a distinct and specified cannabinoid profile or a specific texture/viscosity depending on how the final product is intended to be used. Fine tuning the machine's temperature and pressure parameters allows the manufacturer to hone the output and achieve a specifically desired product.

The CO2 oil extraction has several advantages over other methods. First, CO2 is non-toxic and is Generally Regarded As Safe (GRAS) by the FDA for use in food products. Other extraction solvents, such as hydrocarbon based propellants like propane and butane, hexane and pentane, or ethanol/ alcohol mixtures require additional processing beyond the extraction process in order to ensure the product is safe for consumption. With CO2 oil extraction, no toxins, heavy metals or hydrocarbon materials come in contact with the extracted oils. The spent material is also free of residual contaminates so it can be re-used as well. Second, CO2 is non-flammable. It does not require costly explosion-proof facilities. Third, CO2 is "cold." Using CO2, cannabis oil extractions can be done at temperatures that are native to the plant, minimizing thermal degradation of the plant material and the extracted oil. Fourth CO2 is "tunable." Specifically, the solvency power of CO2 can be adjusted by increasing or decreasing pressures and/or temperatures. Fifth, CO2 is inexpensive and readily available. CO2 oil extraction systems recirculate and subsequently recover 95% of the CO2 used in each extraction. Finally, CO2 is environmentally friendly. It does not contribute to the overall atmospheric CO2 levels.

While the CO2 extraction method is the current preferred method of concentrated cannabis oil extraction, there are multiple methods of producing concentrated cannabis oil. Future technologies may lead to more efficient means of production of concentrated cannabis oil in the future.

After cannabis oil is extracted, a preferred additional step called "winterization" or "de-waxing" should be carried out. Winterization is a post-processing technique used for extracted cannabis oils. While it is not a requirement for the extraction of essential oils, it is sometimes preferred when manufacturing products for vape pens and edibles. Winterization further removes plant waxes, fats, and lipids from the extracted CO2 oil, leaving a thinner, less viscous, and slightly more concentrated product. Ethanol and below-freezing temperatures are used to separate, harden, and remove all remaining waxy materials. The ethanol is then distilled off using the above mentioned rotary evaporator or other distillation technique.

All of the aforementioned methodologies create a cannabis oil product that lends itself to powderization through the addition of starch-based emulsifiers. As the cannabis industry matures and new technologies emerge, new extraction methods will also apply in the powderization of essential cannabis oils and may be useful in the method described herein.

Decarboxylation

There are over 400 chemical compounds that define the chemical makeup of the cannabis plant. THC and CBD are the two most commonly identified compounds, and their symbiotic relationship gives the cannabis plant its many healing attributes. THC content levels are of the utmost importance from the viewpoint of producers of cannabis products. Cultivators, extractors, and edibles manufacturers alike, all regard THC content as the critical aspect that lends (increased) value to their product.

Δ-9-Tetrahydrocannabinol (THC), the main psychoactive component within the chemical makeup of the cannabis plant, is not readily available for consumption and absorption by a user, because in nature the THC exists as carboxylate acid, namely Tetrahydrocannabinolic acid (THCA). THCA is not itself a psychoactive compound, however, studies have shown that it embodies properties such as anti-inflammation, anti-emetic, and neuroprotective aspects. Typically, removal of the carboxyl group is accomplished by a chemical reaction when heat is applied to the THCA, such as when cannabis plant material is smoked. This step is referred to as "decarboxylation" and it must be carried out at some point before or during the consumption of cannabis oil in order for the THC to be available to the consumer.

Edibles producers, if they do not purchase already decarboxylated cannabis oil, face the added task of decarboxylation of their cannabis material before (or after) infusing their products and sending them to market. Otherwise, the edible items, while still containing numerous beneficial cannabinoids, will not induce the intended psychoactive properties. This is because consumers are understandably not expected to smoke or vape an infused brownie or chocolate bar. Instead, the THCA must have already been converted to THC within the infused product, so that ingestion produces the desired effect.

This decarboxylation process can be accomplished in a variety of different ways and at any level of processing. Raw flower, bud or trim can be decarboxylated (without being smoked and before being processed down into concentrates) as can raw concentrates again, without being smoked or vaped and before being infused into edibles. It is up to the extractor or the edibles manufacturer at which point to decarboxylate their cannabis material, and this decision will be made on the basis of time, cost, availability, feasibility, and convenience.

The most effective tool for decarboxylation of cannabis is a vacuum oven. Conventional ovens will also work, but their temperatures fluctuate significantly, and keeping a steady, precise temperature, not an average temperature, is key to successful decarboxylation. Vacuum ovens also allow for the cannabis to decarboxylate at a relatively low temperature for a longer period of time. Keeping the temperature relatively low also helps prevent boiling off some of the other non-psychoactive yet highly beneficial cannabinoids in the cannabis material. For example, using a conventional oven to decarboxylate cannabis at a temperature of 240 degrees Fahrenheit for 60 minutes will convert most, if not all, of the THCA content into THC. However, in the process, the medicinally beneficial terpenoids and flavonoids with much lower evaporation points will have been boiled off, resulting in the loss of many of the believed and suspected health benefits from these compounds. Rather, using a vacuum oven to decarboxylate cannabis at 120 degrees Fahrenheit for 24 hours will convert THCA into THC and generally preserve the terpene profile.

Powderization

The powderization of cannabis begins with cannabis oil. Essential oils are extracted from the cannabis plant into their pure or raw oil form. These extracted oils can then be powderized by adding starch-based emulsifiers such as maltodextrin. In addition, it is important to note that before beginning any powderization, cannabinoid content, particularly the THC percentage by weight, should be known and verified through lab testing.

Typically, extracted oils from the cannabis plant retain a high viscosity. High-viscosity oils are difficult to manage and their properties contribute to loss and waste in a factory setting. To remedy this, gently warming the oil via water bath transforms the extracted oil into a manageable, low-viscosity liquid. To accomplish this, fill a vessel, such as a pot or laboratory water bath that is large enough to fit the jar or container containing the extracted cannabis oil, with water. Carefully place the jar of oil, preferably uncovered, into the water, making sure not to let any water spill into the oil. Keeping the lid on the jar may cause pressure to build in the container if any bubbles should form. The water level should reach at least halfway up the outside of the oil container.

Place the water bath on low heat to slowly and gently warm the water and therefore, the oil. Slowly and gently heating the oil via water bath ensures an even application of heat and prevents the oil from burning. Preferably, the oil and water are heated over time in accordance with the table and graph shown in FIGS. 3A-C and 4, showing exemplary heating times and temperatures for approximately one pound of cannabis oil being heated in approximately one gallon of water in a water bath. Preferably, the cannabis oil is heated until it is approximately the same viscosity as a light syrup or teriyaki sauce. This preferred oil viscosity is achieved at between 80 and 100 degrees Fahrenheit oil temperature. Even more preferably, the preferred oil viscosity is achieved at between 84 and 90 degrees Fahrenheit oil temperature.

Once the oil has been gently heated and is at a manageable, liquid viscosity, maltodextrin or other suitable human-consumable powder is mixed with the oil using an industrial blender. Commercial equipment, as opposed to hand-blending or a home appliance, is preferred to mix the oil and starch together to ensure total and complete even absorption of the powder by the oil. If the oil and starch are not thoroughly mixed, this will cause "hot spots," i.e., uneven disbursement of the oil in the powderized oil, leading to inaccurate dosing.

To obtain the preferred ratio of maltodextrin to oil, compute the following: at least 3 grams of maltodextrin is preferred for every ⅛ gram of oil to create a powder that will completely emulsify in a hot liquid. First, obtain the weight of the oil in grams. Divide the total weight of the oil into ⅛ ths of a gram. To do this, simply divide the weight of the oil by 0.125. Multiply this quotient by 3 to get the total grams of maltodextrin required to powderize the oil. (grams of oil/0.125)*3=grams of maltodextrin to be mixed with oil.

Lower ratios of maltodextrin to oil may also be useful. For example, a ratio of maltodextrin to cannabis oil of as low as 3 grams of maltodextrin to a half-a-gram of oil will still allow the oil to be powderized in such a way that, when added to hot water, the powder will dissolve and most of the oil will emulsify, with some visible oil droplets at the surface of the hot water. To reiterate, the more powder (emulsifier) that is used, the easier it is for the material to be stable in water and the less oil "residue" will be found on top of the liquid or sides of beverage container, resulting in a more commercially viable product due to its more pleasing appearance, taste and complete mixing.

Once a manufacturer has determined the weight of the maltodextrin required to powderize, slowly add the heated oil to the pre-weighted maltodextrin. Mix thoroughly using an industrial blender until the powder achieves complete uniformity. Visual inspection of the powder should conclude that there are no visible "spots" of oil and the powder is a uniform golden-yellowish color.

From this point, the powder is sent to the lab for testing and dosage corroboration.

Lab tests will aid in honing exact dosage amounts and should always be deferred to when dosing infused products with a specified amount of cannabis. However, to estimate what a single dose will be (use 15 mg THC, for example) the following math can be applied, assuming the original oil was lab tested and THC % is known:

- Multiply the THC percentage of the oil by 10. For example, if the THC percentage is known to be 65%, multiply 65*10 to get 650. This is the number of milligrams of THC for every one gram of oil.
- Since we have determined that a single dose is 15 mg THC, we divide the product from above by 15 to obtain the number of single doses per gram of oil.
- 650/15=43.3. This means there are 43.3 15 mg doses in a single gram of oil at 65% THC.

(65*10=650 mg/g)÷15 mg dose=43.3 doses/g

Next, to obtain the total number of doses in the entire batch of oil, multiply the number of doses per gram of oil (43.3 above) by the total grams of oil originally used. For example, if we originally powderized 1 lb (454 grams) of oil, we would multiply 43.3*454 to get 19,658.2 total 15 mg doses in the entire batch of (the now powderized) oil.

43.3*454=19,658.2 total 15 mg doses per batch

After determining the total number of doses per batch, simply divide the total weight of the batch by the total number of doses to obtain the weight of a single dose. According to the example above, if we used 454 grams of oil originally, we would have a total powderized weight of 11,350 grams (25 lbs). Dividing this by the total number of doses will give us an approximation of 0.58 grams of powderized oil for a single dose.

11350÷19658.2=0.5774 grams powderized oil in a single 15 mg dose

Due to decimal rounding, these figures, while reasonably accurate, are still approximations and should always be corroborated through lab testing to ensure precise dosage.

Finally, while the above description has been largely directed to the use of maltodextrin, other starch powders, may be used in this process. Additionally, other types of powders fit for human consumption may be used, so long as they absorb the oil when blended together, dissolve when added to a liquid, remain dissolved in that liquid and have no post-mixing separation of the powder and the oil. Examples of other types of viable powders fit for human consumption that may be used in accordance with the disclosure herein include but not limited to: whey protein isolate (both dairy-based and plant-based), xanthan gum/guar gum (guaran), gum Arabic, mono- and diglycerides, and carboxymethyl cellulose (cellulose gum), lecithin powder (sometimes called soy lecithin), MCT Oil powder, Molasses powder, powdered sugars such as dextrose, citric acid, anti-caking agents or flow agents such as calcium silicate, silicon dioxide, silica powder, and sodium aluminosilicate, sodium caseinate, centrolene, sodium citrate, dipotassium phosphate, bone meal, calcium phosphate, creatine, L-leucine, magnesium citrate, magnesium oxide, magnesium carbonate, magnesium oxide, magnesium carbonate, calcium phosphate, corn starch, aluminum silicate, stevia leaf extract, yeast, micro-crystalline cellulose, Horny Goat Weed, Ginseng, St. John's Wort, Skullcap Powder, Ginko, Niacin, Resveratrol, Turmeric, L-Arginine, L-Citrulline, L-Theanine, L-Trytophan, and Calcium β-Hydroxy β-Methylbutyrate Monohydrate.

Terpene Oil Powderization and Uses

Terpenes, as discussed herein, are natural aromatic compounds found in both cannabis, and many other plants. Terpenes are generally found in, or as part of, the "essential oil" of a given plant. Terpenes are generally believed to provide many and varying health benefits. However, the terpene profile of any given cannabis strain or extracted cannabis oil is subject to substantial variability. Moreover, some terpenes, which are present in only small amounts in cannabis, may have beneficial properties in higher doses, and are either more plentiful, or are more easily extracted and preserved as essential oil from non-cannabis plants. Thus, per embodiments described herein, it is possible to obtain extracted terpene oil from either cannabis or from non-cannabis sources, and then adjust, modify or stabilize the terpene profile of the forms of powderized cannabis oil described herein. It should be understood that embodiments of the method and composition of matter described below can be practiced with any terpene that is generally in, or can be caused to be in, a liquid form, preferably an oil. With respect to embodiments described herein, the term "terpene oil" should be understood to be any essential oil or liquid containing terpenes or terpenoids, and can be derived from cannabis, or from non-cannabis sources.

Figure 5:
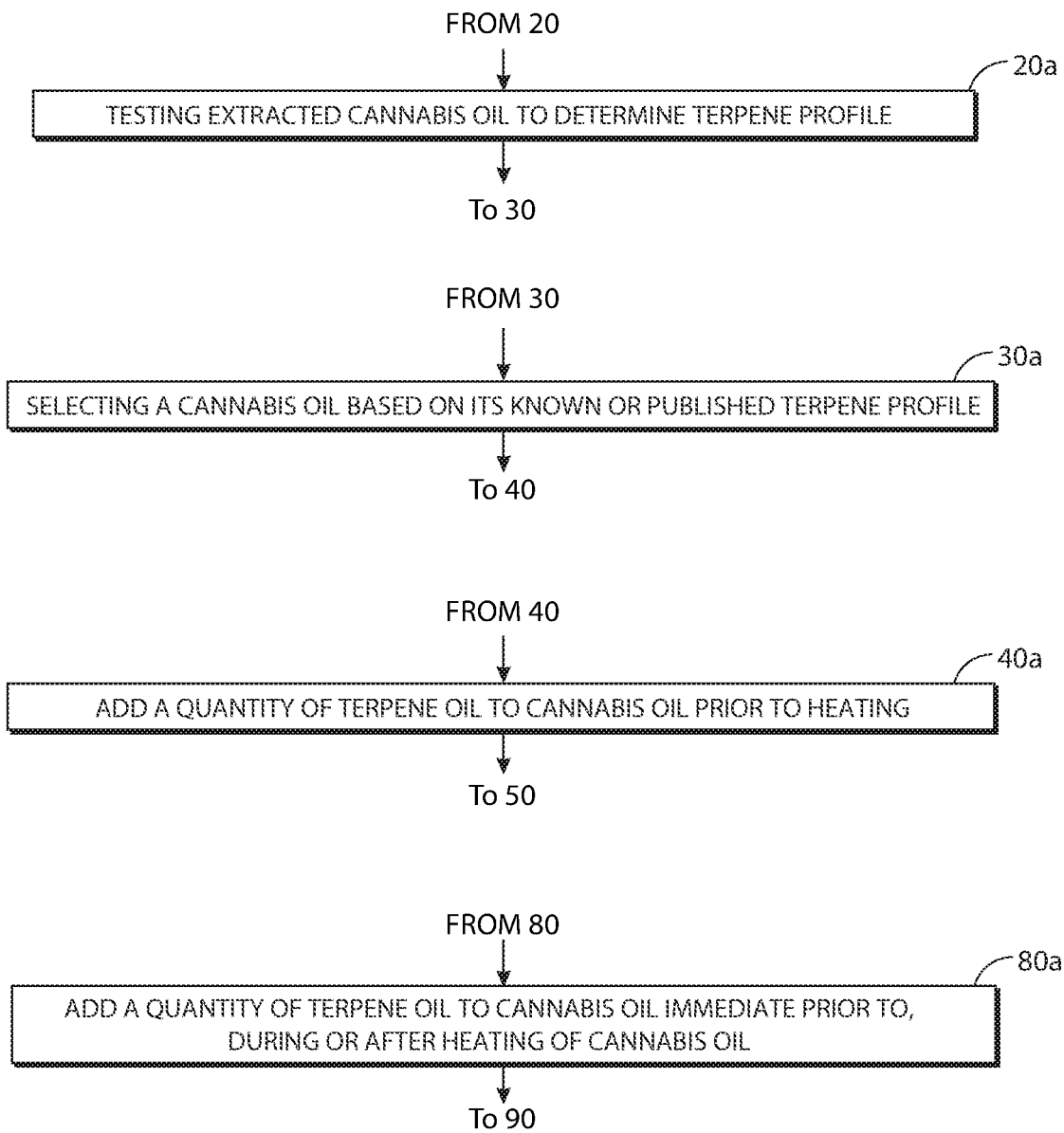
FIG. 5 is a flowchart, to be read in conjunction with FIG. 1, showing additional steps for an embodiment of a cannabis oil powderization process that enables enhancement or manipulation of the terpene profile of the resulting powderized cannabis oil.

With reference to FIG. 5, an embodiment that sets forth optional steps to enable manufacture terpene-modified powderized cannabis oil is provided in which terpenes are added to liquefied heated cannabis oil prior to powderization. This embodiment is referred to herein as the "wet process" and may be understood as an improvement and alternate additional steps to the process discussed with respect to FIG. 1, particularly steps 20, 30, 40 and 80. In embodiments of the wet process, cannabis oil may be tested to determine its terpene profile 20a, as part of step 20. Alternatively, or additionally, cannabis oil may be selected based on its known or published terpene profile 30a, as part of step 30. Then, the manufacturer may decide upon the desired terpene profile of any resultant powderized cannabis oil. It should be understood that this desired terpene profile can be for the purpose of establishing a consistent terpene profile by addressing and fixing varying terpene profiles of commercially available cannabis oil, or it may be or the purpose of custom-blending a terpene profile that is not known with respect to any existing cannabis strain or extracted cannabis oil. Terpene oil may be added at either step 40 or step 80. In one embodiment, terpene oil may be added to a quantity of cannabis oil at room temperature, at step 40a. In general, cannabis oil at room temperature is quite viscous, so addition of terpene oil at step 40a often does not result in adequate blending of the terpene oil and the cannabis oil. In another embodiment, at step 80a, terpene oil may be added to a quantity of cannabis oil either immediately prior to, during, or after step 80, in which the cannabis oil is warmed to reduce its viscosity. Addition of terpene oil at step 80a typically results in a micro emulsion, after blending. Terpene oil may be added, for example, at a ratio of 0.1 gram of terpene oil to 1 gram of cannabis oil. Other ratios may be selected, depending upon the desired resultant terpene profile in the powderized cannabis oil. Further multiple different terpene oils may be added and blended in order to achieve a desired resultant terpene profile in the powderized cannabis oil.

Figure 6:
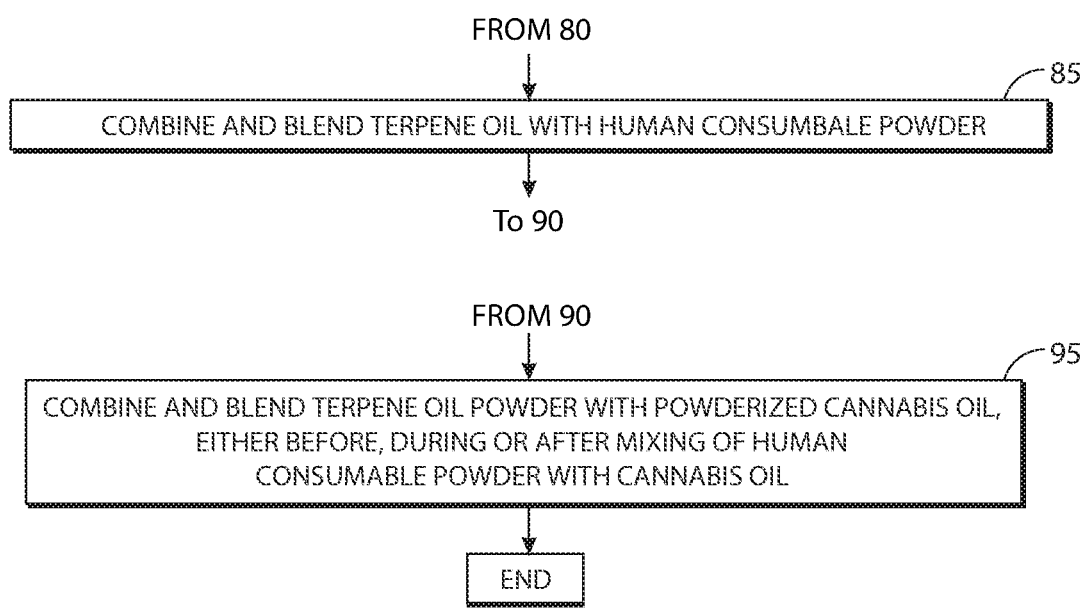
FIG. 6 is a flowchart, to be read in conjunction with FIG. 1, showing additional steps for another embodiment of a cannabis oil powderization process that enables enhancement or manipulation of the terpene profile of the resulting powderized cannabis oil.

With reference to FIG. 6, another embodiment that sets forth additional optional steps to manufacture terpene-modified powderized cannabis oil is provided in which terpene oil is powderized, and then the powderized terpene oil is combined with powderized cannabis oil. This embodiment is referred to herein as the "dry process" and may be understood as an improvement to and additional steps to the process discussed with respect to FIG. 1, particularly step 90. At step 85, terpene oil is combined and blended with a human consumable powder of the types described above, such as, for example, maltodextrin. This blending may be made at any suitable ratio of terpene oil to human consumable powder, so long as the ratio enables consistent absorption of the terpene oil in the powder, so that there are no "hot spots" of unabsorbed terpene oil, or "cold spots" of powder that has not absorbed a meaningful (or any) terpene oil. One exemplar ratio of terpene oil to human consumable powder is 0.125 grams of terpene oil to 3 grams of human consumable powder. Step 85 may be carried out at any time prior to or during step 90 with respect to the process set forth in FIG. 1. For example, step 85 can be performed days or weeks prior to manufacture of powderized cannabis oil, so that terpene oil powder is pre-made and in stock. Further, by pre-manufacturing the terpene oil powder (and/or a variety of different terpene oil powders, using different terpenes, or combinations of terpenes), custom blends of powderized cannabis oil with a modified terpene profile to be manufactured, by combining the desired types and amounts of terpene oil powder(s) for blending with powderized cannabis oil as it is manufactured or shortly thereafter. Alternatively, step 85 can be performed just prior to, or at the same time as steps 80 or 90. It should also be understood that the human consumable powder used for the manufacture of the powderized cannabis oil and the human consumable powder used for the manufacture of the terpene oil powder can be the same type of powder, e.g., maltodextrin, or they may be different types of powder so long as they meet the definition of human consumable powder set forth herein.

Lower ratios of human consumable powder, such as for example maltodextrin, to terpene oil may also be useful. For example, a ratio of human consumable powder to terpene oil of as low as 3 grams of maltodextrin to a half-a-gram of terpene oil will still allow the terpene oil to be powderized in such a way that, when added to hot water, the powder will dissolve and most of the oil will emulsify, with some visible oil droplets at the surface of the hot water. To reiterate, the more human consumable powder (emulsifier) that is used, the easier it is for the material to be stable in water and the less oil "residue" will be found on top of the liquid or sides of beverage container, resulting in a more commercially viable product due to its more pleasing appearance, taste and complete mixing.

At step 95, terpene oil powder is blended with the desired quantity of human consumable powder and warmed cannabis oil, to result in powderized cannabis oil with a modified terpene profile. Step 95 may be carried out either before, during or after step 90. Additionally, more than one type of terpene oil powder may be blended in order to achieve a desired terpene profile.

Using the embodiments of either the wet or dry process described herein, various kinds of custom-blended powderized cannabis oil with modified terpene profiles may be created to address specific consumer preferences and medical needs. Examples include but are not limited to:

Anti-Convulsant Mix: Mix Terpineol and Isopulegol oils in equal parts, combine with human consumable powder, such as maltodextrin, in a ratio of 0.0626 g oil to 3 g of human consumable powder.

Anti-Depressant Mix: Mix Linalool and B-Pinene oils in equal parts, combine with human consumable powder, such as maltodextrin, in a ratio of 0.0626 g oil to 3 g of human consumable powder.

Anti-Inflammatory Mix: Mix a ratio of 0.125 g of a-Pinene oil to 3 g of human consumable powder, such as maltodextrin.

Alternate Anti-Inflammatory Mix: Mix a ratio of 0.125 g of a combined terpene oil to 3 g of human consumable powder, such as maltodextrin, wherein the combined terpene oil includes, by weight, 24.7% Terpinene, 16.6% B-Pinene, 5.7% Limonene, 5.6% Ocimene, and 4.7% A-Pinene.

Anti-Anxiety and Anti-Depression Mix: Mix in a ratio of 0.125 g of B-Caryophyllene oil to 3 grams of human consumable powder, such as maltodextrin.

Enhanced Delivery Mix: Eucalyptol can pass the blood-brain barrier and hence can be used as a carrier to deliver drugs to the brain, increase bioavailability of cannabinoids and possibly other compounds. Thus, mix a ratio of 0.125 g of Eucalyptol oil to 3 g of human consumable powder, such as maltodextrin. Then, consider adding additional other medicinal or herbal compounds or components.

Alternate Enhanced Delivery Mix: Borneol can pass the blood-brain barrier and hence can be used as a carrier to deliver drugs to the brain, increase bioavailability of cannabinoids and possibly other compounds. Thus, mix a ratio of 0.125 g of Borneol oil to 3 g of human consumable powder, such as maltodextrin. Then, consider adding additional other medicinal or herbal compounds or components.

Sedative Mix: Terpinoline has been shown to have a sedative effect. Thus, mix a ratio of 0.125 g of Terpinoline oil to 3 g of human consumable powder, such as maltodextrin.

Alternative Sedative Mix: Nerolidol has been shown to have a sedative effect. Thus, mix a ratio of 0.125 g of Nerolidol to 3 g of human consumable powder, such as maltodextrin.

Sleep Mix: Mix Linalool and Myrcene oils in equal parts, combine with human consumable powder, such as maltodextrin, in a ratio of 0.0626 g oil to 3 g of human consumable powder, combined with a 1:1 ratio of THC to CBD powder combined at a ratio of 0.125 g of cannabis oil to 3 g of human consumable powder, such as maltodextrin.

Muscle Relaxing Mix: Myrcene has been shown to have a muscle relaxing effect. Thus, mix a ratio of 0.125 of Myrcene oil to 3 g of human consumable powder, such as maltodextrin.

It should also be understood that processes such as that described with respect to terpene oil can also be used with respect to cannabinoids that are present in only small or minute amounts in the cannabis plant. For example, extracted or purified THCV oil may be combined with a human consumable powder, such as for example maltodextrin, and then added to powderized cannabis oil using either the wet process or the dry process described above.

In still further embodiments, other types of powders that are fit for human consumption and are known or suspected nutritional or herbal supplements may be used, including but not limited to Piperine and Hops powder.

Lecithin powder, sometimes called soy lecithin powder, is a Phospholipid that can create a slow release effect for THC and/or CBD when taken in a capsule, thereby increasing bioavailability of the THC and/or CBD.

In still further embodiments, other types of powders that are fit for human consumption and are known or suspected nutritional or herbal supplements may be used, including but not limited to powdered Piperine and Hops powder.

Piperine is a component of black pepper and in anecdotally rumored in the cannabis community to alleviate the "anxiety effect" that some individuals experience when consuming THC. It is also believed by some researchers that Piperine has the effect of increasing bioavailability or absorption of various active ingredients. For example, see the article "Bioavailability of phytochemicals and its enhancement by drug delivery systems," by Farrukh Aquil, et. al., published in *Cancer Lett.* 2013 Jun. 28; 334(1): 133-141. doi:10.1016/j.canlet.2013.02.032, which is hereby incorporated by reference in its entirety. For further example, see the article "Piperine-pro-nanolipospheres as a novel oral delivery system of cannabinoids: Pharmacokinetic evaluation in healthy volunteers in comparison to buccal spray administration," by Irina Cherniakov, et. al., *Journal of Controlled Release*, Volume 266, 28 Nov. 2017, Pages 1-7, which is hereby incorporated by reference in its entirety, but states in part that:

"THC and CBD are prone to extensive first pass mechanisms. These absorption obstacles render the molecules with low and variable oral bioavailability. To overcome these limitations we designed and developed the advanced pro-nanolipospheres (PNL) formulation. The PNL delivery system is comprised of a medium chain triglyceride, surfactants, a co-solvent and the unique addition of a natural absorption enhancer: piperine. Piperine was selected due to its distinctive inhibitory properties affecting both Phase I and Phase II metabolism. This constellation self emulsifies into nano particles that entrap the cannabinoids and the piperine in their core and thus improve their solubility while piperine and the other PNL excipients inhibit their intestinal metabolism . . . Single oral administration of the piperine-PNL formulation resulted in a 3-fold increase in Cmax and a 1.5-fold increase in AUC for THC when compared to Sativex®. For CBD, a 4-fold increase in Cmax and a 2.2-fold increase in AUC was observed. These findings demonstrate the potential this formulation has in serving as a standardized oral cannabinoid formulation. Moreover, the concept of improving oral bioavailability described here, can pave the way for other potential lipophilic active compounds requiring enhancement of their oral bioavailability."

For still further example, an anecdotal article posted online by a user of cannabis at http://www.rollitup.org/t/increasing-cannabis-effects-through-enzyme-inhibition-easy-get-more-from-your-meds.648452/stated that:

"So much thought lately goes into concentrating marijuana, . . . but very little is seemingly given to the active compounds methods of action. This is a shame, because there are lots of things you can do to enhance and increase cannabis' effects in the body that are completely independent of the cannabis itself . . . . There are a number of foods and OTC medications that can inhibit CYP 2C9 strongly: Piperine (Long/Black/West African Pepper) . . . you will need only about ⅓ to ½ as much marijuana as you regularly do. It's surprising how well this works. It's especially handy if you dose orally—instead of getting relief for only an hour or two, an oral dose can last all day!"

Myrcene, as discussed above, is a terpene that is found naturally in cannabis, as well as in other plants and fruits, such as hops and mangoes. It has been anecdotally rumored in the cannabis community for many years that a cannabis consumer can increase the effects of THC or CBD by consuming a mango, e.g., eating a mango immediately prior to smoking marijuana. As explained in the article "Taming THC: potential cannabis synergy and phytocannabinoid-terpenoid entourage effects", Br. J. Pharmacol. 2011 August; 163(7): 1344-1364. doi: 10.1111/j.1476-5381.2011.01238.x:

"Myrcene is a recognized sedative as part of hops preparations (*Humulus lupulus*), employed to aid sleep in Germany (Bisset and Wichtl, 2004). Furthermore, myrcene acted as a muscle relaxant in mice, and potentiated barbiturate sleep time at high doses (do Vale et al., 2002). Together, these data would support the hypothesis that myrcene is a prominent sedative terpenoid in cannabis, and combined with THC, may produce the 'couch-lock' phenomenon of certain chemotypes that is alternatively decried or appreciated by recreational cannabis consumers."

Powdered Hops is high in Myrcene and may also be useful as described and claimed herein. Further, powdered Myrcene either extracted from plant materials or synthetically created, may also be available.

Additionally, certain embodiments contemplated herein may include the addition of supplemental ingredients listed below, for the purposes of supplementing, enhancing, aiding or complementing the effects of the active components of the cannabis oil. Each of these supplemental ingredients may be added to the powderized cannabis oil, either as a dry ingredient to the powder, prior to the mixing of the cannabis oil, or after. Moreover, each of these supplemental ingredients may be included in a capsule or tablet, along with the powderized cannabis oil. Supplemental ingredients, along with their anticipated effects, are as follows:

Sleep Aids
- Melatonin: helps control your natural sleep-wake cycle. Some research suggests that melatonin supplements might be helpful in treating jet lag or reducing the time it takes to fall asleep—although the effect is typically mild. Side effects can include headache and daytime sleepiness.
- Diphenhydramine hydrochloride: sedating antihistamine. Side effects might include daytime drowsiness, dry mouth, blurred vision, constipation and urinary retention.
- Doxylamine succinate: sedating antihistamine. Side effects are similar to those of diphenhydramine.
- Valerian Root: Supplements made from this plant are sometimes taken as sleep aids. Although a few studies indicate some therapeutic benefit, other studies haven't found the same benefits. Valerian generally does not appear to cause side effects.

Energy Supplements
- Vitamin B12.
- Caffeine.

Health and Wellness
- Vitamin C—immune support.
- Zinc—immune support.
- Iron—blood health.
- Calcium—bone health.
- Ginkgo Biloba—brain function.
- Co-Q 10—heart health.

Magnesium—bone health.
St. John's Wort—mood leveler.
Biotin—hair and skin health.
Potassium—cell and nerve function.
Fish Oil—heart health.
L-lysine—skin and tissue health.
Taurine—cardiovascular and muscle health, retina and nervous system health.
Collagen powder—joint and bone health and enhance skin health.

General Illness Remedies
Ibuprofen—pain reliever/fever reducer.
Acetaminophen—pain reliever/fever reducer.
Naproxen NaCl—pain reliever/fever reducer.
Aspirin—pain reliever/fever reducer.
Phenylephrine—nasal decongestant.
Loratadine—antihistamine.
Chlorpheniramine maleate—antihistamine.
Cetirizine HCL—antihistamine.
Fexofenadine HCL—antihistamine.
Guaifenesin—cough suppression.
Dextromethorphan—cough suppression.
Famotidine—acid reducer.
Omeprazole—acid reducer.
Esomeprazole—acid reducer.
Lansoprazole—acid reducer
Pamabrom—diuretic
Manuka Honey powder—antibacterial Uses of the Powderized Cannabis Oil The resulting stable, emulsifiable and flavorless concentrated cannabis oil infused powder may be added to or used in many different applications where the addition of cannabis is desired. For example, the powderized cannabis oil may be used in a wide variety of recipes, hot beverages, tea bags and single serve beverage brewing cartridges, which are often referred to by the trademark "K-cups," bottled beverages that are brewed hot, food additive packets intended to be poured directly into hot beverages, tea bags, coffee pods/filters, ground coffee and instant coffee packages, as well as added to or used in the manufacture of lozenges, candies, tablets and capsules. The amounts of concentrated cannabis oil infused powder added to the aforementioned applications will be produced in varying doses of THC and CBD depending on the desired amount. In certain embodiments, forms of the powderized cannabis may be compressed for tablets, or encapsulated in capsules.

To achieve a specific THC/CBD mg dosage in each product, mixing ratios of CO2 extracted cannabis oil and maltodextrin will depend on the potency, determined by lab testing, of the cannabis oil, but are generally preferred to be at least three grams of maltodextrin to each one-eighth of a gram of cannabis oil. In addition, depending on the viscosity of the oil, more or less maltodextrin will be used. Take, for example, a hypothetical batch of CO2 cannabis oil tested at a concentration of 48% THC and 1.7% CBD. This means that every gram of oil at this concentration contains 480 mg of THC and 170 mg of CBD. So, to make one 40 mg product, we mix 0.08 g (40÷480) of oil with approximately 2 grams of maltodextrin to create an infused powder containing 40 mg THC. For an 80 mg product, we mix 0.17 g (80÷480 rounded) of oil with approximately 4 grams of maltodextrin to create the concentrated cannabis oil infused maltodextrin powder containing 80 mg THC.

The infused powder applies to a 40 mg THC dose or an 80 mg THC dose (for example) that can be inserted into a coffee filter/pod directly with the coffee grounds, in a tea bag with the tea leaves, inside a single serve "k-cup" in the filter with the coffee grounds or tea leaves or below the filter at the bottom of the "k-cup," inserted in an instant coffee grounds pack or placed in a packet, like sugar or aspartame, which can be poured directly into a hot beverage or hot soup and or baked into food items. All of the aforementioned applications will have the same efficacy, regardless of how the concentrated cannabis oil infused maltodextrin powder is ingested by a user. Varying amounts of concentrated cannabis oil infused maltodextrin powder can be used to make THC or CBD doses ranging from 5 mg to 200 mg, and up, and preferably between 5 mg and 150 mg, depending on medical need, state restrictions, and consumer demand.

The creation of the concentrated cannabis oil infused maltodextrin powder will take place in a sterile, food grade manufacturing facility. The concentrated cannabis oil infused maltodextrin powder will be precisely added to each of the aforementioned applications through automated, mass production equipment with nitrogen sealed packaging to ensure an 18 month shelf life.

As demonstrated, exact recipes will depend on lab tests and the exact concentrations of each batch of CO2 oil. However, these slight variations in concentration will be compensated for during the manufacturing process. In addition, the product is odorless and tasteless, so there will be no discernible difference from unit to unit from the consumer's perspective. Each k-cup, tea bag, the concentrated cannabis oil infused maltodextrin powder packet or ground coffee will deliver the consistent quality and expected experience to the end user.

Application/Recipes

Additionally, a number of exemplar recipes for making edible products and beverages using cannabis oil powder of the present invention are provided as follows, but are not intended to be limiting.

Gelatin Shots (makes 24×10 mg servings):
Ingredients
1 pkg. (3 oz.) gelatin mix
3 cups hot water
1 cup cold water
240 mg THC powder
24 single-serve paper cups
Directions
Heat 3 cups water to boiling. Stir in gelatin mix and THC powder. Stir for 2 min or until completely dissolved. Add 1 cup cold water. Continue to stir and keep solution well mixed while dispensing equal amounts (approx. ½ oz.) into 24 single-serve paper cups.
Refrigerate approximately 4 hours or until gelatin becomes firm, before consuming.

Cookies, most varieties (makes 2-dozen 10 mg cookies):
Ingredients
Any cookie recipe
240 mg THC powder
Directions
Follow recipe as directed. Mix/dissolve THC powder with vegetable oil and/or eggs. If recipe does not call for veg. oil/eggs, THC powder should be added first in the batter-making process. Mix batter VERY thoroughly (with a hand blender) before dispensing 24 equal-sized (about ½ tbsp.) spoonful's onto cookie sheet. Bake as directed.

Brownies, most varieties (makes 12×10 mg brownies):
Ingredients
Any brownie recipe
120 mg THC powder Directions Follow recipe as directed. Mix/dissolve THC powder with vegetable oil and/or eggs. If recipe does not call for veg. oil/eggs, THC powder should be added first in the batter-making process. Mix batter VERY thoroughly (with a hand blender) before dispensing into baking tray. Bake as directed. Cut into 12 equal-sized 10 mg squares.

Cupcakes/Muffins, most varieties (makes 12×10 mg cupcakes):

Ingredients

Any cupcake/muffin recipe 120 mg THC powder

Directions

Follow recipe as directed. Mix/dissolve THC powder with vegetable oil and/or eggs. If recipe does not call for veg. oil/eggs, THC powder should be added first in the batter-making process. Mix batter VERY thoroughly (with a hand blender) before dispensing equal amounts of batter into cupcake/muffin tray. Bake as directed.

Pancakes (makes 12×10 mg pancakes):

Ingredients

Any pancake recipe 120 mg THC powder

Directions

Follow recipe as directed. Mix/dissolve THC powder with vegetable oil and/or eggs. If recipe does not call for veg. oil/eggs, THC powder should be added first in the batter-making process. Mix batter VERY thoroughly (with a hand blender) before dispensing equal amounts of batter onto heated skillet.

Cake (makes 12×10 mg cake slices):

Ingredients

Any cake recipe 120 mg THC powder

Directions

Follow recipe as directed. Mix/dissolve THC powder with vegetable oil and/or eggs. If recipe does not call for veg. oil/eggs, THC powder should be added first in the batter-making process. Mix batter VERY thoroughly (with a hand blender) before dispensing batter into baking tray. Bake as directed. Cut into equal-sized 10 mg slices.

Instant Oatmeal (one serving):

Ingredients 1 pkg. (1.5 oz) instant oatmeal

⅔ cup water or milk 10 mg THC powder

Directions

Empty contents of package into a microwave-safe bowl. Add THC powder to dry oats. Add ⅔ cup water or milk and stir. Microwave as directed. Remove from microwave and stir thoroughly before enjoying.

Make-Your-Own K-Cups (single serve coffee brewing cartridge cups):

Ingredients 10 mg THC powder 1 tbsp. coffee or tea

Directions

Before placing the filter, place THC powder at the bottom of the single serve coffee brewing cartridge cup. Place filter. Fill with coffee or tea (approx. 1 tbsp.). Secure lid. Place into any K-cup brewer and operate as instructed. THC powder will permeate certain coffee filters better than others. To avoid any loss of THC powder by filtration, it is recommended to bypass the filter by placing the powder material at the bottom of the cup.

Beverages (e.g., water, lemonade, tea, coffee, hot cocoa, soda, juice, milk, cider, bouillon (broth), shakes and smoothies, etc.):

Ingredients 10 mg THC powder

Consumer's beverage of choice

Directions

Mix/dissolve THC powder into HOT water or HOT beverage

If beverage is not intended to be ingested hot, the liquid may be poured over ice or refrigerated/cooled as desired once the THC powder has already been dissolved. The THC powder will remain emulsified in the beverage after cooling, however, the initial application of the powder must be into a HOT liquid, due to the unique emulsification properties of the powderized oil.

When infusing carbonated beverages that may require the application of a concentrated syrup, it is best to initially heat the syrup and dissolve the THC powder into the heated syrup, then add water and carbonate.

THC powder can be added just as any other ingredient when blending a milkshake or fruit smoothie without the application of any heat. Obviously, the application of heat to a shake or smoothie would deteriorate the quality of such beverages. Adding the THC powder during the blending process lends itself well to making infused shakes/smoothies without heat and does not produce issues like clumping/sticking of oil onto sides of container, if sufficient blending is carried it, i.e. at least 2-3 minutes.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments disclosed.

What is claimed is:

1. A method for making powderized cannabis oil with a modified terpene profile, comprising the steps of:

selecting a cannabis oil;

measuring a desired quantity of the cannabis oil and selecting a first human consumable powder;

measuring a desired quantity of the first human consumable powder to achieve a ratio of the first human consumable powder to the cannabis oil, by weight;

wherein the ratio of the first human consumable powder to the cannabis oil, by weight, is at least three grams of first human consumable powder to every one-half of a gram of cannabis oil;

mixing the cannabis oil and the first human consumable powder until the cannabis oil is evenly absorbed by the first human consumable powder to create a powderized cannabis oil;

selecting a terpene oil;

measuring a desired quantity of the terpene oil; selecting a second human consumable powder;

mixing the terpene oil and the second human consumable powder until the terpene oil is evenly absorbed by the second human consumable powder to create a terpene oil powder; and mixing the powderized cannabis oil and the terpene oil powder until the terpene oil powder is evenly distributed throughout the powderized cannabis oil, wherein the first and second human consumable powders are two or more powders selected from the group consisting of molasses, calcium silicate, silicon dioxide, sodium aluminosilicate and sodium caseinate.

2. The method of claim 1, wherein the ratio of the first human consumable powder to the cannabis oil, by weight, is at least three grams of the first human consumable powder to every one-eighth of a gram of cannabis oil.

3. The method of claim 1, wherein the terpene oil is selected from the group consisting of Myrcene, Limonene, Caryophyllene, Pinene, Terpineol, Borneo, Delta-3-Carene, Linalool, Pulegone, Cineole, Ocimene, Terpinoline, Guaiol, Bisabolol, Nerolidol, Humulene, Geraniol, Thujone and Valencene.

* * * * *